United States Patent
Resnick et al.

(10) Patent No.: US 11,286,310 B2
(45) Date of Patent: Mar. 29, 2022

(54) METHODS AND APPARATUS FOR FALSE POSITIVE MINIMIZATION IN FACIAL RECOGNITION APPLICATIONS

(71) Applicant: 15 Seconds of Fame, Inc., Santa Monica, CA (US)

(72) Inventors: Adam Resnick, Boca Raton, FL (US); Ruslan Sabitov, Jersey City, NJ (US); Brett Joshpe, New York, NY (US)

(73) Assignee: 15 SECONDS OF FAME, INC., Santa Monica, CA (US)

( * ) Notice: Subject to any disclaimer, the term of this patent is extended or adjusted under 35 U.S.C. 154(b) by 22 days.

(21) Appl. No.: 16/865,878

(22) Filed: May 4, 2020

(65) Prior Publication Data
US 2020/0262931 A1 Aug. 20, 2020

Related U.S. Application Data

(63) Continuation of application No. 15/299,934, filed on Oct. 21, 2016, now Pat. No. 10,654,942.

(Continued)

(51) Int. Cl.
*C07K 16/40* (2006.01)
*G06K 9/00* (2006.01)
(Continued)

(52) U.S. Cl.
CPC ........ *C07K 16/40* (2013.01); *A61K 39/39591* (2013.01); *A61K 47/26* (2013.01);
(Continued)

(58) Field of Classification Search
CPC ........... G06K 9/00288; G06K 9/00765; G06K 9/209; G06K 9/6215; G06K 9/6269; G06K 2209/27; A61K 47/26; C07K 16/18
(Continued)

(56) References Cited

U.S. PATENT DOCUMENTS 5,144,685 A 9/1992 Nasar et al.
6,142,876 A 11/2000 Cumbers
(Continued)

FOREIGN PATENT DOCUMENTS

CN 102047249 A 5/2011
JP 2003-317100 11/2003
(Continued)

OTHER PUBLICATIONS

Extended European Search Report for European Application No. 16794804.1, dated Jul. 31, 2019, 14 pages.
(Continued)

*Primary Examiner* — Mark Roz
(74) *Attorney, Agent, or Firm* — Carlson, Gaskey & Olds, P.C.

(57) ABSTRACT

An apparatus can include a processor that can receive location data from a user device, and store the location data in a user profile data structure also storing facial recognition data. The processor can also receive at least one image, and can identify a location based at least in part on a set of characteristics within the at least one image. The processor can, for each user profile data structure stored in a database, compare location data in that user profile data structure to the location. The processor can, when the location data of the user profile data structure and the location match, conduct facial recognition to determine whether the user associated with the user profile data structure can be identified in the at least one image. The processor can then associate the at least one image with the user profile data structure if the user can be identified.

23 Claims, 7 Drawing Sheets

Related U.S. Application Data

(60) Provisional application No. 62/244,419, filed on Oct. 21, 2015.

(51) Int. Cl.
*G06K 9/62* (2006.01)
*C07K 16/18* (2006.01)
*A61K 39/395* (2006.01)
*A61K 47/26* (2006.01)

(52) U.S. Cl.
CPC .......... *C07K 16/18* (2013.01); *G06K 9/00288* (2013.01); *G06K 9/00744* (2013.01); *G06K 9/00765* (2013.01); *G06K 9/6215* (2013.01); *G06K 2209/27* (2013.01)

(58) Field of Classification Search
USPC ........................................................ 382/118
See application file for complete search history.

(56) References Cited

U.S. PATENT DOCUMENTS

| | | |
|---|---|---|
| 6,532,345 B1 | 3/2003 | Gluck |
| 6,591,068 B1 | 7/2003 | Dietz |
| 6,745,186 B1 | 6/2004 | Testa et al. |
| 6,819,783 B2 | 11/2004 | Goldberg et al. |
| 7,023,367 B1 | 4/2006 | Shniberg et al. |
| 7,035,440 B2 | 4/2006 | Kaku |
| 7,260,587 B2 | 8/2007 | Testa et al. |
| 7,330,875 B1 | 2/2008 | Parasnis et al. |
| 7,376,276 B2 | 5/2008 | Shniberg et al. |
| 7,391,886 B1 | 5/2008 | Clark et al. |
| 7,472,134 B2 | 12/2008 | Kaku |
| 7,494,061 B2 | 2/2009 | Reinhold |
| 7,526,106 B1 | 4/2009 | Clark et al. |
| 7,532,811 B2 | 5/2009 | Sauder |
| 7,552,228 B2 | 6/2009 | Parasnis et al. |
| 7,561,723 B2 | 7/2009 | Goldberg et al. |
| 7,619,660 B2 | 11/2009 | Grosvenor |
| 7,684,651 B2 | 3/2010 | Tang et al. |
| 7,783,085 B2 | 8/2010 | Perlmutter et al. |
| 7,800,646 B2 | 9/2010 | Martin |
| 7,860,347 B2 | 12/2010 | Tang et al. |
| 7,881,968 B2 | 2/2011 | David |
| 7,907,755 B1 | 3/2011 | Perlmutter et al. |
| 7,953,690 B2 | 5/2011 | Luo et al. |
| 7,965,908 B2 | 6/2011 | Hayashi |
| 7,966,223 B2 | 6/2011 | David |
| 7,995,806 B2 | 8/2011 | Goh et al. |
| 8,014,572 B2 | 9/2011 | Xiao et al. |
| 8,055,029 B2 | 11/2011 | Petrescu et al. |
| 8,144,944 B2 | 3/2012 | Ishii |
| 8,189,880 B2 | 5/2012 | Wen et al. |
| 8,204,437 B1 | 6/2012 | Rothschild |
| 8,233,679 B2 | 7/2012 | Perlmutter et al. |
| 8,254,699 B1 | 8/2012 | Zhao et al. |
| 8,260,674 B2 | 9/2012 | David |
| 8,279,323 B2 | 10/2012 | Ishii |
| 8,284,990 B2 | 10/2012 | Ma et al. |
| 8,306,284 B2 | 11/2012 | Goldberg et al. |
| 8,315,463 B2 | 11/2012 | Gallagher et al. |
| 8,325,999 B2 | 12/2012 | Kapoor et al. |
| 8,341,145 B2 | 12/2012 | Dodson et al. |
| 8,392,957 B2 | 3/2013 | Holt et al. |
| 8,406,481 B2 | 3/2013 | Goldberg |
| 8,422,739 B2 | 4/2013 | Ianculescu et al. |
| 8,560,625 B1 | 10/2013 | Hardman et al. |
| 8,630,956 B2 | 1/2014 | Arisawa et al. |
| 8,723,962 B2 | 5/2014 | Herring et al. |
| 8,782,709 B2 | 7/2014 | Wang et al. |
| 8,799,277 B2 | 8/2014 | Park et al. |
| 8,825,872 B2 | 9/2014 | Reisman |
| 8,831,275 B2 | 9/2014 | Goldberg |
| 8,885,960 B2 | 11/2014 | Sauve et al. |
| 8,898,464 B2 | 11/2014 | Bono et al. |
| 8,928,760 B2 | 1/2015 | Schultz et al. |
| 8,942,533 B2 | 1/2015 | Wiklof |
| 8,949,619 B2 | 2/2015 | Parry et al. |
| 8,957,981 B2 | 2/2015 | Fredlund et al. |
| 9,007,420 B1 | 4/2015 | Passe |
| 9,008,724 B2 | 4/2015 | Lord |
| 9,104,907 B2 | 8/2015 | Whitehill et al. |
| 9,131,147 B2 | 9/2015 | Quardordt et al. |
| 9,189,682 B2 | 11/2015 | Salvador et al. |
| 9,213,885 B1 | 12/2015 | Schneiderman |
| 9,317,530 B2 | 4/2016 | Papakipos et al. |
| 9,386,180 B2 | 7/2016 | Oki |
| 9,396,354 B1 | 7/2016 | Murphy et al. |
| 9,420,315 B2 | 8/2016 | Melanson |
| 9,531,998 B1 | 12/2016 | Farrell et al. |
| 9,652,663 B2 | 5/2017 | Lau et al. |
| 9,668,002 B1 | 5/2017 | Baron et al. |
| 9,712,800 B2 | 7/2017 | St. Clair |
| 9,723,334 B2 | 8/2017 | Melanson |
| 9,852,364 B2 | 12/2017 | Liu et al. |
| 9,967,596 B2 | 5/2018 | Melanson |
| 10,019,136 B1 | 7/2018 | Ozog |
| 10,027,726 B1 | 7/2018 | Ozog |
| 10,027,727 B1 | 7/2018 | Ozog |
| 10,094,655 B2 | 10/2018 | Sabitov et al. |
| 10,121,061 B2 | 11/2018 | Dickinson et al. |
| 10,591,281 B2 | 3/2020 | Sabitov et al. |
| 10,654,942 B2 | 5/2020 | Resnick et al. |
| 2003/0023452 A1 | 1/2003 | Novais et al. |
| 2003/0086123 A1 | 5/2003 | Torrens-Burton |
| 2003/0118216 A1 | 6/2003 | Goldberg |
| 2004/0008872 A1 | 1/2004 | Goldberg |
| 2004/0156535 A1* | 8/2004 | Goldberg ............ H04N 1/00172 382/115 |
| 2005/0117022 A1 | 6/2005 | Marchant |
| 2005/0254505 A1 | 11/2005 | Chang et al. |
| 2005/0283497 A1 | 12/2005 | Nurminen et al. |
| 2006/0020630 A1 | 1/2006 | Stager et al. |
| 2006/0171603 A1 | 8/2006 | Jung et al. |
| 2006/0229063 A1 | 10/2006 | Koch |
| 2007/0003113 A1 | 1/2007 | Goldberg |
| 2008/0091723 A1 | 4/2008 | Zuckerberg et al. |
| 2008/0201327 A1 | 8/2008 | Seth |
| 2008/0211904 A1 | 9/2008 | Kato et al. |
| 2008/0243861 A1 | 10/2008 | Wassingbo et al. |
| 2008/0260212 A1 | 10/2008 | Moskal et al. |
| 2008/0310688 A1 | 12/2008 | Goldberg |
| 2009/0043725 A1 | 2/2009 | Gutta |
| 2009/0074258 A1 | 3/2009 | Cotgreave |
| 2009/0103887 A1 | 4/2009 | Choi et al. |
| 2009/0185723 A1 | 7/2009 | Kurtz et al. |
| 2009/0316961 A1 | 12/2009 | Gomez Suarez et al. |
| 2010/0036875 A1 | 2/2010 | Miezianko et al. |
| 2010/0060727 A1 | 3/2010 | Steinberg et al. |
| 2010/0150407 A1 | 6/2010 | Cheswick |
| 2010/0158315 A1 | 6/2010 | Martin |
| 2010/0172550 A1 | 7/2010 | Gilley et al. |
| 2010/0207721 A1 | 8/2010 | Nakajima et al. |
| 2010/0216441 A1 | 8/2010 | Larsson et al. |
| 2010/0241658 A1 | 9/2010 | Rathurs et al. |
| 2011/0013810 A1 | 1/2011 | Engstrom et al. |
| 2011/0022529 A1 | 1/2011 | Barsoba et al. |
| 2011/0064281 A1 | 3/2011 | Chan |
| 2011/0066743 A1 | 3/2011 | Hurley et al. |
| 2011/0142016 A1 | 6/2011 | Chatterjee |
| 2011/0182482 A1 | 7/2011 | Winters et al. |
| 2011/0182485 A1 | 7/2011 | Shochat et al. |
| 2011/0188713 A1 | 8/2011 | Chin et al. |
| 2011/0211736 A1 | 9/2011 | Krupka et al. |
| 2011/0211737 A1 | 9/2011 | Krupka et al. |
| 2011/0238755 A1 | 9/2011 | Khan et al. |
| 2011/0257985 A1 | 10/2011 | Goldstein |
| 2011/0282860 A1 | 11/2011 | Baarman et al. |
| 2011/0307399 A1 | 12/2011 | Russell et al. |
| 2012/0008837 A1 | 1/2012 | Goldberg et al. |
| 2012/0027256 A1 | 2/2012 | Kiyohara et al. |
| 2012/0056722 A1 | 3/2012 | Kawaguchi |
| 2012/0250950 A1 | 10/2012 | Papakipos et al. |

(56) References Cited

U.S. PATENT DOCUMENTS

| | | |
|---|---|---|
| 2012/0278395 A1 | 11/2012 | Garcia |
| 2013/0040660 A1 | 2/2013 | Fisher et al. |
| 2013/0089243 A1 | 4/2013 | Sauve et al. |
| 2013/0117365 A1 | 5/2013 | Padmanabhan et al. |
| 2013/0136316 A1 | 5/2013 | Grassel et al. |
| 2013/0188844 A1 | 7/2013 | Goldberg |
| 2013/0194438 A1 | 8/2013 | Sweet, III et al. |
| 2013/0223744 A1 | 8/2013 | Ramanujapuram et al. |
| 2013/0265448 A1 | 10/2013 | Li |
| 2013/0265450 A1 | 10/2013 | Barnes, Jr. |
| 2013/0269013 A1 | 10/2013 | Parry et al. |
| 2013/0286223 A1 | 10/2013 | Latta et al. |
| 2014/0028201 A1 | 1/2014 | Chang |
| 2014/0064576 A1 | 3/2014 | Gong et al. |
| 2014/0250126 A1 | 9/2014 | Baldwin et al. |
| 2014/0267618 A1 | 9/2014 | Esteban et al. |
| 2014/0289534 A1 | 9/2014 | Parry et al. |
| 2014/0342330 A1 | 11/2014 | Freeman et al. |
| 2014/0350840 A1 | 11/2014 | D'Argenio et al. |
| 2014/0361974 A1 | 12/2014 | Li et al. |
| 2015/0057995 A1 | 2/2015 | Neumann et al. |
| 2015/0062334 A1 | 3/2015 | Dickinson et al. |
| 2015/0066920 A1 | 3/2015 | Barta |
| 2015/0081785 A1 | 3/2015 | Angelsmark et al. |
| 2015/0081791 A1 | 3/2015 | Jacobs |
| 2015/0124107 A1 | 5/2015 | Muriello |
| 2015/0169946 A1 | 6/2015 | Needleman |
| 2015/0172787 A1 | 6/2015 | Geramifard |
| 2015/0172853 A1 | 6/2015 | Liu et al. |
| 2015/0181379 A1 | 6/2015 | Pai et al. |
| 2015/0227609 A1* | 8/2015 | Shoemaker ............ G06F 16/532 707/737 |
| 2015/0227780 A1 | 8/2015 | Tussy |
| 2015/0227782 A1 | 8/2015 | Salvador et al. |
| 2015/0254723 A1 | 9/2015 | Chand et al. |
| 2015/0286856 A1 | 10/2015 | Garcia et al. |
| 2015/0304368 A1 | 10/2015 | Vaccari et al. |
| 2015/0347827 A1 | 12/2015 | Dickinson et al. |
| 2016/0026853 A1 | 1/2016 | Wexler et al. |
| 2016/0071101 A1 | 3/2016 | Winarski |
| 2016/0073010 A1 | 3/2016 | Cronin et al. |
| 2016/0105772 A1 | 4/2016 | Cohen |
| 2016/0150124 A1 | 5/2016 | Panda et al. |
| 2016/0182816 A1 | 6/2016 | Luk et al. |
| 2016/0191434 A1 | 6/2016 | Rice |
| 2016/0205358 A1 | 7/2016 | Dickinson |
| 2017/0192401 A1 | 7/2017 | Wexler et al. |
| 2018/0025220 A1 | 1/2018 | Dickinson et al. |
| 2018/0189571 A1 | 7/2018 | Seo et al. |
| 2018/0234709 A1 | 8/2018 | Melanson |
| 2018/0300554 A1 | 10/2018 | Kansara |
| 2018/0341835 A1 | 11/2018 | Siminoff |
| 2019/0034710 A1 | 1/2019 | Dickinson et al. |
| 2019/0043351 A1 | 2/2019 | Yang et al. |
| 2019/0045207 A1 | 2/2019 | Chen et al. |
| 2019/0087646 A1 | 3/2019 | Goulden et al. |
| 2019/0137261 A1 | 5/2019 | Sabitov et al. |
| 2019/0179960 A1 | 6/2019 | Im et al. |
| 2020/0217645 A1 | 7/2020 | Sabitov et al. |

FOREIGN PATENT DOCUMENTS

| | | |
|---|---|---|
| JP | 2010-009389 | 1/2010 |
| JP | 2012-507761 | 3/2012 |
| WO | WO 2009/123711 | 10/2009 |
| WO | WO 2011/017653 | 2/2011 |
| WO | WO 2011/097041 | 8/2011 |
| WO | WO 2012/112992 | 8/2012 |
| WO | WO 2012/134756 | 10/2012 |
| WO | WO 2012/142054 | 10/2012 |
| WO | WO 2012/149397 | 11/2012 |
| WO | WO 2014/043738 | 3/2014 |
| WO | WO 2014/100519 | 6/2014 |
| WO | WO 2015/030911 | 3/2015 |
| WO | WO 2015/031863 | 3/2015 |
| WO | WO 2015/085246 | 6/2015 |

OTHER PUBLICATIONS

Extended Search Report for European Application No. 16825245.0, dated Mar. 20, 2019, 8 pages.

International Search Report and Written Opinion for International Application No. PCT/US2016/042489, dated Oct. 21, 2016, 7 pages.

International Search Report and Written Opinion for International Application No. PCT/US2016/058189, dated Jan. 13, 2017, 8 pages.

Office Action for U.S. Appl. No. 15/211,261, dated Nov. 30, 2017, 15 pages.

Supplementary European Search Report for European Application No. 16794804.1, dated Apr. 30, 2019, 17 pages.

Office Action for U.S. Appl. No. 15/299,934, dated May 24, 2018, 15 pages.

Final Office Action for U.S. Appl. No. 15/299,934, dated Dec. 6, 2018, 17 pages.

Office Action for U.S. Appl. No. 15/299,934, dated Jul. 26, 2019, 17 pages.

Office Action issued by the Japanese Patent Office for Application No. 2018-521489, dated Dec. 9, 2019, 11 pages including English translation.

Office Action issued by the Japanese Patent Office for Application No. 2018-520402, dated Jun. 10, 2020, 7 pages including English translation.

Office Action issued by the Brazilian Patent Office for Application No. BR112018007979-0, dated Jul. 14, 2020, 5 pages including informal English translation.

FotoTiger Facial Recognition Webpage, dated Nov. 18, 2018, retrieved online on Mar. 25, 2020, at https://thenextweb.com/apps/2014/11/18/fototiger-facial-recognition-app-android-puts-photos/, 4 pages.

Amy Held, Google App Goes Viral Making an Art Out of Matching Faces to Paintings, Jan. 15, 2018, NPR.org, Retrieved from the Internet: https://www.npr.org/sections/thetwo-way/2018/01/15/578151195/google-app-goes-viral-making-an-art-out-of-matching-faces-to-paintings, 8 pages.

Ashley Gurbal Kritzer, Tampa Bay Business Journal, Vinik—backed Seattle startup brings new tech to Amalie Arena for Lightning games, Feb. 5, 2016. Retrieved from the Internet: http://www.bizjournals.com/tampabay/blog/morning-edition/2016/02/vinik-backed-seattle-startup-brings-new-tech-to.html,A171, 4 pages.

Barr et al., "Face Recognition From Video: a Review", Draft 17 International Journal of Pattern Recognition and Artificial Intelligence, 2012, 56 pages, Retrieved from the Internet Nov. 11, 2013: URL:http://www3.nd.edu/-kwb/BarrEtAllJPRAI 2012.pdf.

Ben Coxworth, "Software could determine where a video was shot, based on scenery and ambient sound," Feb. 19, 2015, Gizmag.com, retrieved from the internet at http://www.gizmag.com/video-geolocation- IQorithms/36172 on Oct. 6, 2015, 3 pages.

Chris Welch, How to Stop Facebook from Looking for You With Face Recognition, Mar. 27, 2018. Retrieved from the Internet: https://www.theverge.com/2018/3/27/17165150/facebook-face-recognition-how-to-turn-off-disable, 6 pages.

Co tree, Selfies—Automatic selfie by multiple faces detection, Released Mar. 26, 2015, Retrieved from the Internet: https://itunes.apple.com/US/app/selfies-automatic-selfie-by/id976846726?mt=8, 2 pages.

Colin Morris, HomeAdvisor co-founders launch photo marketplace powered by facial recognition, Built in Austin, Jan. 22, 2016. Retrieved from the Internet: http://www.builtinaustin.com/2016/01/22/waldo-photos-5-million-seed-round, 3 pages.

Collen Kriel, Alibaba shows off facial recognition to secure mobile payments, Mar. 16, 2015. Retrieved from the Internet: http://siliconangle.com/blog/2015/03/16/alibaba-shows-off-facial-recognition-to-secure-mobile-payments/, 5 pages.

ComputerWorld, Face Recognition app FindFace may make you want to take down all your online photos, May 18, 2016, 3 pages.

(56) References Cited

OTHER PUBLICATIONS

Dave Brooks, Nathan Hubbard's Plan to 'Rival' Ticketmaster Makes Big Claims, But Offers Few Details, May 4, 2018, Retrieved from the Internet: https://www.billboard.com/articles/business/8454599/nathan-hubbard-ticketmaster-rival, 3 pages.
Dave Gershgorn, A New App Automatically Sends That Group Photo to Your Friends, Popular Science, Mar. 7, 2016. Retrieved from the Internet: http://www.popsci.com/new-app-automatically-sends-that-group-photo-to-your-friends, 2 pages.
Doug Bolton, FindFace app which uses facial recognition to identify strangers on social media takes Russia by storm, May 18, 2016. http://www.independent.co.uk/life-style/gadgets-and-tech/news/findface-vk-app-social-media-facial-recognition-android-ios-a7035556.html, 2 pages.
Edgar Cervantes, Facebook will recognize you in photos where your face is not showing, Android Authority, Jun. 23, 2015. Retrieved from the Internet: http://www.androidauthority.com/facebook-recognize-photos-without-face-618957/, 5 pages.
Fanpics, Tell Your Story. Retrieved Nov. 30, 2016 from the Internet: https://www.fanpics.com/about, 3 pages.
Ironic Sans, Idea: Fun with facial recognition, Jan. 11, 2007. Retrieved from the Internet: http://www.ironicsans.com/2007/01/idea_fun_with_facial_recogniti.html, 5 pages.
Jack Alexander, Next Generation of iPhones to 'Revolutionize' Photography, May Include Sony's 3D Technology and Advanced Facial Recognition, Dec. 29, 2018. Retrieved from the Internet: https://fstoppers.com/news/next-generation-iPhones-revolutionize-photography-may-include-sonys-3D-322630, 2 pages.
James Vincent, "Facial Recognition Smart Glasses Could Make Public Surveillance Discreet and Ubiquitous," Updated Jun. 12, 2019. Retrieved from the Internet: URL: https://www.theverge.com/2019/6/10/18659660/facial-recognition-smart-glasses-sunglasses-surveillance-vuzix-nntc-uae, 4 pages.
Julian Mitchell, Staples Center, AEG and Fanpics Partner to Put Fans At the Center of Major Sports Moments, May 27, 2015. Retrieved from the Internet: http://www.forbes.com/sites/julianmitchell/2015/05/27/staples-center-and-fanpics-team-up-putting-fans-at-the-center-of-major-sports-moments/2/#60ccf4ceba08, 5 pages.
Justin Lee, Securus patents facial recognition system for video visitation sessions, Biometric Update.com. Jun. 16, 2015. Retrieved from the Internet: http://www.biometricupdate.com/201506/securus-patents-facial-recognition-system-for-video-visitation-sessions, 3 pages.
Katy Daniells, FaceLook: Coca-Cola's Facial Recognition App, Aug. 2, 2011. Retrieved from the Internet: http://www.digitalbuzzblog.com/facelook-coca-colas-facial-recognition-app/, 12 pages.
Kim Brunhuber, Facial recognition tech is allowing stores to reward customers, CBC News, May 2, 2016, 5 pages.
Knoto, published 2016, Retrieved Dec. 12, 2016 from the Internet: http://knoto.com/, 5 pages.
Lamdba Labs, API Documentation. Retrieved from the Internet on Jan. 17, 2019 at https://lambdal.com/api-documentation, 2 pages.
Magtoapp, Inc., iTunes Preview, Celebtwin: Celebrity Look Alike Lite. Updated Jul. 5, 2016, Retrieved Dec. 2, 2016 from the Internet: https://itunes.apple.com/US/app/celebtwin-celebrity-look-alike/id381722077?mt=8, 2 pages.
Michelle Ma, Moving cameras talk to each other to identify, track pedestrians, Nov. 12, 2014. Retrieved from the Internet: http://www.washington.edu/news/2014/11/12/moving-cameras-talk-to-each-other-to-identify-track-pedestrians/, 6 pages.
Mori Rothman, Bringing facial recognition technology to the 'kiss cam' at sporting events, PBS Newshour, Sep. 24, 2013, Retrieved from the Internet: http://www.pbs.org/newshour/rundown/dhs-taps-into-crowd-cam-for-facial-recognition-research/, 2 pages.
Naaman, et al. Stanford University, "Leveraging Context to Resolve Identity in Photo Albums", 2005, 10 pages.
OSnap, Tutorial 2: Time-Lapse—Daily Self Portrait, Retrieved Nov. 30, 2016 from the Internet: http://www.osnapphotoapp.com/tutorial2.php, 6 pages.
Penny Crosman, Biometric Tipping Point: USAA Deploys Face, Voice Recognition, Feb. 3, 2015. Retrieved from the Internet: http://www.americanbanker.com/news/bank-technology/biometric-tipping-point-usaa-deploys-face-voice-recognition-1072509-1.html?zkPrintable=1&nopagination=1, 7 pages.
Peter Holley, This Patent Shows Amazon May Seek to Create a 'Database of Suspicious Persons' Using Facial-Recognition Technology, Dec. 18, 2018, Washingtonpost.com, Retrieved from the Internet: https://www.washingtonpost.com/technology/2018/12/13/this-patent-shows-amazon-may-seek-create-database-suspicious-persons-using-facial-recognition-technology/?utm_term=.476ede26a7f8, 3 pages.
Planet biometrics, Facial recognition startup will scour web for user images, Feb. 3, 2016. Retrieved from the Internet: http://www.planetbiometrics.eom/article-details/i/4100/desc/facial-recognition-startup-will-scour-web-for-user-images/, 2 pages.
PR Newswire, FacialNetwork Releases New Demo of Facial Recognition App NameTag On Google Glass, Receives Cease and Desist from Facebook, Sep. 10, 2014, Retrieved from Internet: http://www.prnewswire.com/news-releases/facialnetwork-releases-new-demo-of-facial-recognition-app-nametag-on-google-glass-receives-cease-and-desist-from-facebook-274649581.html, 4 pages.
PR Newswire, Waldo Photos Closes $5 Million Seed Funding Round Led by Upfront Ventures, Jan. 21, 2016. Retrieved from the Internet: https://www.prnewswire.com/news-releases/waldo-photos-closes-5-million-seed-funding-round-led-by-upfront-ventures-300206555.html, 2 pages.
PR Rocket, Photo-Sharing Image Recognition Tools Advocacy Campaign Launched by ScanMyPhotos.com, Mar. 8, 2016. Retrieved from the Internet: http://www.pressreleaserocket.net/photo-sharing-image-recognition-tools-advocacy-campaign-launched-by-scanmyphotos-com/419781/, 3 pages.
Rachel Metz, A New Way to Use Facial Recognition to Find Photos of You, Feb. 2, 2016, MIT Technology Review. Retrieved from the Internet: https://www.technologyreview.com/s/600690/a-new-way-to-use-facial-recognition-to-find-photos-of-you/, 3 pages.
Rob Price, Snapchat has figured out a way to use facial recognition tech to protect people's privacy, Business Insider, Jul. 19, 2016. Retrieved from the Internet: http://www.businessinsider.com/new-snapchat-patent-uses-facial-recognition-tech-protect-privacy-photos-blurring-emojis-2016-7, 6 pages.
Ryan Whitwam, Facebook developing way to fingerprint the camera you used to take a photo, Sep. 20, 2015. Retrieved from the Internet: http://www.geek.com/news/facebook-developing-way-to-fingerprint-the-camera-you-used-to-take-a-photo-1634542/, 3 pages.
Sarah Perez, Lambda Labs Is Launching A Facial Recognition API For Google Glass, May 23, 2013. Retrieved from the Internet: http://techcrunch.com/2013/05/23/lambda-labs-is-launching-a-facial-recognition-api-for-google-glass/, 15 pages.
Sarah Perez, Waldo Raises $5 Million For A Photo-Finding Platform Targeting Professional Photographers & Events, TechCrunch, Jan. 21, 2016. Retrieved from the Internet: Dec. 2, 2016 at https://techcrunch.com/2016/01/21/waldo-raises-5-million-for-a-photo-finding-platform-targeting-professional-photographers-events/, 9 pages.
Seatrade Cruise News, The Image Group provides photo buyers mobile-friendly instant gratification, Nov. 8, 2015. Retrieved from the Internet: http://www.seatrade-cruise.com/news/news-headlines/image-provides-photo-buyers-mobile-friendly-instant-gratification.html, 2 pages.
Taylor Soper, Ex-Microsoft manager raises cash from sports team owners to enhance the fan experience at live games, GeekWire, Feb. 4, 2016. Retrieved from the Internet: http://www.geekwire.com/2016/ex-microsoft-manager-raises-cash-sports-team-owners-enhance-fan-experience-live-games/, 16 pages.
Texas TechPulse, Waldo Photos: Finding Your Photos In the Proverbial Haystack, Feb. 3, 2016. Retrieved from the Internet: http://www.texastechpulse.com/waldo_photos_finding_your_photos_in_the_proverbial_haystack/s-0063812.html, 3 pages.
The Ghost in the Camera, How facial recognition technology mines your face for information, Feb. 2016, 1 page.
Vlad Savov, Sony Promises Better Face Identification Through Depth-Sensing Lasers, Jan. 2, 2019. Retrieved from the Internet: https://www.theverge.com/2019/1/2/18164881/sony-tof-laser-depthsensing-3d-camera-report, 3 pages.

(56) References Cited

OTHER PUBLICATIONS

Zhang et al., "Image Based Localization in Urban Environments", 3D Data Processing, Visualization, and Transmission, Third International Symposium On, IEEE, PI, pp. 33-40 (2006).
ZoOmTM, The World's First Secure Selfie 3D Authentication App, Announced by FacialNetwork, Jul. 8, 2015. Retrieved from the Internet: http://www.marketwatch.com/story/zoomtm-the-worlds-first-secure-selfie-3d-authentication-app-announced-by-facialnetwork-2015-07-08, 9 pages.
First Office Action and Search Report for Chinese Application No. 201680074728.6 dated Jun. 18, 2021.

* cited by examiner

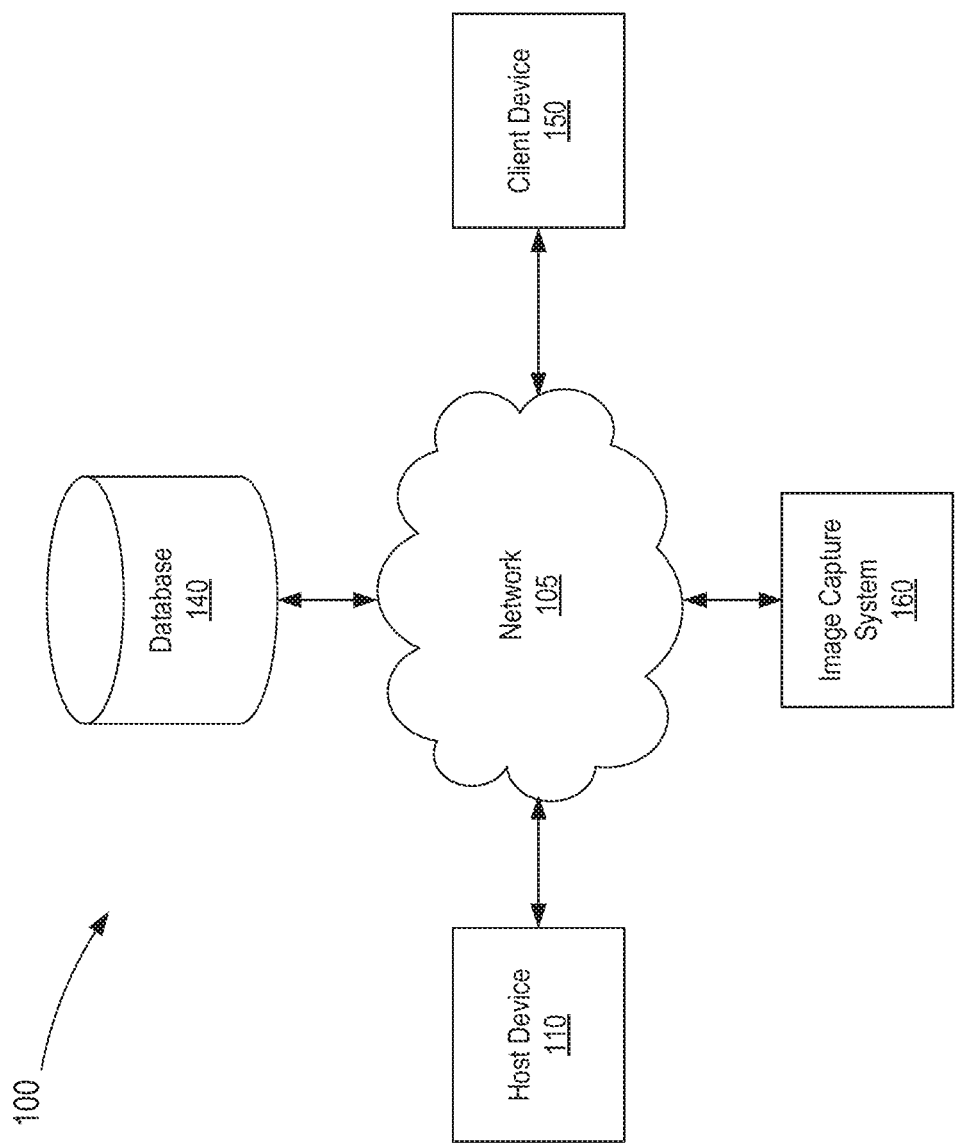

METHODS AND APPARATUS FOR FALSE POSITIVE MINIMIZATION IN FACIAL RECOGNITION APPLICATIONS

CROSS-REFERENCE TO RELATED APPLICATION

This application is a continuation of U.S. application Ser. No. 15/299,934, filed Oct. 21, 2016, entitled "Methods and Apparatus for False Positive Minimization in Facial Recognition Applications", which claims priority to and the benefit of U.S. Provisional Application Ser. No. 62/244,419, filed Oct. 21, 2015, entitled "Methods and Apparatus for False Positive Minimization in Facial Recognition Applications". The entire contents of each of which is hereby incorporated by reference in its entirety.

BACKGROUND

The embodiments described herein relate generally to facial recognition and video analytics, and more particularly, to apparatus and methods for false positive minimization in facial recognition applications.

Increases in the availability and capability of electronic devices such as cameras, tablets, smartphones, etc. have allowed some people to take pictures and/or capture video of their experiences. For example, the inclusion and improvement of cameras in smartphones, tablets, and/or other similar devices have led to increases in those devices being used to take pictures (e.g., photographic data, image data, etc.) and videos (e.g., video stream data). While, it has become easier for some people to take pictures and/or videos of their experiences, in some instances, there can still be challenges in including the desired parties (including the person who would otherwise be taking the picture or video). Moreover, a person generally has to remember and/or have the chance to take the picture and/or video, and failing to do can result in a lost opportunity.

In some instances, venues and/or events such as sporting events, concerts, rallies, graduations, and/or the like have cameras that can take pictures and/or video of those in attendance. In some instances, however, analyzing, parsing, and/or otherwise making the pictures and/or video stream available can use a relatively large amount of resources, can be inaccurate, and/or can fail to provide associated contextual data or the like. More specifically, in some instances, it can be difficult to verify that a particular person detected in a picture, was actually in the location captured in the picture, due to false positives obtained from using facial recognition alone to identify people in pictures.

Thus, a need exists for improved apparatus and methods for using contextual and location data for minimizing false positives at, for example, public events.

SUMMARY

In some implementations, an apparatus can include a memory and a processor operatively coupled to the memory. The processor can, at a first time, receive location data from a user device, and can store the location data in a user profile data structure. The user profile data structure can include facial recognition data of a user of the user device associated with the user based on at least one of two-dimensional facial recognition analytics, three-dimensional facial recognition analytics, or convolutional neural nets (CNN). The processor can receive, at a second time different from the first time, at least one image from an image capture device. The processor can identify a location based at least in part on a set of characteristics within the received at least one image, and can retrieve, from a database, multiple of user profile data structures including the user profile data structure. The processor can, for each user profile data structure from the multiple user profile data structures, compare location data in that user profile data structure to the location. The processor can, when the location data of the user profile data structure and the location are within a predetermined distance of each other, determine whether the user associated with the user profile data structure can be identified in the at least one image. For example, the processor can analyze the at least one image with respect to the facial recognition data of the user based on at least one of the two-dimensional facial recognition analytics, the three-dimensional facial recognition analytics, or the CNN to identify a facial recognition confidence score. The processor can then associate the at least one image with the user profile data structure based on the facial recognition confidence score meeting a predetermined criterion.

BRIEF DESCRIPTION OF THE DRAWINGS

FIG. 1A is a schematic illustration of a recognition system according to an embodiment.

DETAILED DESCRIPTION

Figure 1B:
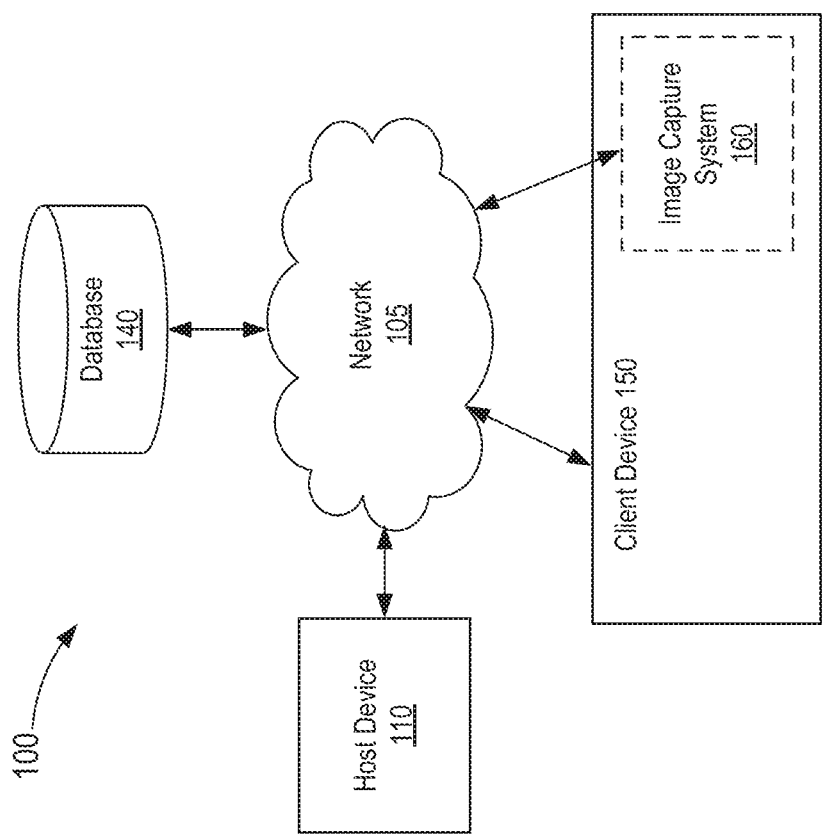
FIG. 1B is a schematic illustration of a recognition system according to another embodiment.

In some implementations, an apparatus can include a memory and a processor operatively coupled to the memory. The processor can, at a first time, receive location data from a user device, and can store the location data in a user profile data structure. The user profile data structure can include facial recognition data of a user of the user device associated with the user based on at least one of two-dimensional facial recognition analytics, three-dimensional facial recognition analytics, or convolutional neural nets (CNN). The processor can receive, at a second time different from the first time, at least one image from an image capture device. The processor can identify a location based at least in part on a set of characteristics within the received at least one image, and can retrieve, from a database, multiple user profile data structures including the user profile data structure. The processor can, for each user profile data structure from the multiple user profile data structures, compare location data in that user profile data structure to the location. The processor can, when the location data of the user profile data structure and the location are within a predetermined distance of each other, determine whether the user associated with the user profile data structure can be identified in the at least one image. For example, the processor can analyze the at least one image with respect to the facial recognition data of the user based on at least one of the two-dimensional facial recognition analytics, the three-dimensional facial recognition analytics, or the CNN to identify a facial recognition confidence score. The processor can then associate the at least one image with the user profile data structure based on the facial recognition confidence score meeting a predetermined criterion The embodiments described herein relate to detecting a user in media based on facial recognition data and location information. In some embodiments, a method of image analysis includes receiving, at a host device and from a client device via a network, a signal indicative of user check-ins at a location. The user can check in via her mobile device. An image capture device can capture media (e.g., photographs, videos, audio, and/or similar content) that may include the user. The host device can use the scenery and/or other background information in the media (e.g., after processing the media via image processing techniques) to determine a particular location at which the media was captured. The host device can also receive location information for the image capture device, e.g., to verify the location of the image capture device and/or the location the media detects. The host device can match the location detected in the media, with location data of users who have checked in, to determine which users have checked in at a location close to where the media was captured. The host device can then perform image processing on the media to determine whether the users who checked in close to the location in the media appear in the media. The host device can send notifications to users who the host device detects in the media. In this manner, the host device can reduce the number of users to search for in a particular media file, and reduce false positives by tying both the user's location and the user's appearance to the data obtained from the media . . . .

As used in this specification, the singular forms "a," "an" and "the" include plural referents unless the context clearly dictates otherwise. Thus, for example, the term "a module" is intended to mean a single module or a combination of modules, "a network" is intended to mean one or more networks, or a combination thereof.

As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a field-programmable gate array (FPGA), an application specific integrated circuit (ASIC), a digital signal processor (DSP)) and/or software-based module (e.g., a module of computer code stored in memory and/or executed at the processor) capable of performing one or more specific functions associated with that module.

The embodiments and methods described herein can use facial recognition data to (1) search for one or more images of a registered user (e.g., a person who's facial recognition data is predetermined) in a video stream and (2) provide a video stream including contextual data to a client device associated with the user (e.g., a smartphone, tablet, computer, wearable electronic device, etc.). Facial recognition generally involves analyzing one or more images of a person's face to determine, for example, salient features of his or her facial structure (e.g., cheekbones, chin, ears, eyes, jaw, nose, hairline, etc.) and then defining a qualitative and/or quantitative data set associated with and/or otherwise representing the salient features. One approach, for example, includes extracting data associated with salient features of a person's face and defining a data set including geometric and/or coordinate based information (e.g., a three dimensional (3-D) analysis of facial recognition data). Another approach, for example, includes distilling image data into qualitative values and comparing those values to templates or the like (e.g., a two-dimensional (2-D) analysis of facial recognition data). In some instances, another approach can include any suitable combination of 3-D analytics and 2-D analytics.

Some facial recognition methods and/or algorithms include Principal Component Analysis using Eigenfaces (e.g., Eigenvector associated with facial recognition), Linear Discriminate Analysis, Elastic Bunch Graph Matching using the Fisherface algorithm, Hidden Markov model, Multilinear Subspace Learning using tensor representation, neuronal motivated dynamic link matching, convolutional neural nets (CNN), and/or the like or combination thereof. Any of the embodiments and/or methods described herein can use and/or implement any suitable facial recognition method and/or algorithm or combination thereof such as those described above.

FIG. 1A is a schematic illustration of a video recognition system 100 according to an embodiment. In some instances, the video recognition system 100 (also referred to herein as "system") can be used to present a video stream of a user based at least in part on facial recognition data. At least a portion of the system 100 can be, for example, represented and/or described by a set of instructions or code stored in a memory and executed in a processor of an electronic device (e.g., a host device, a server or group of servers, a personal computer (PC), a network device, etc.) and/or the like. For example, in some embodiments, a host device can receive a signal associated with a request to register facial recognition data associated with a user and in response, can store the facial recognition data in a database. Similarly, the host device can receive a signal associated with video stream data. In some instances, one or more processors of the host device can then execute a set of instructions or code, stored in a memory of the host device, associated with analyzing the video stream data to determine if one or more images of the user are present in the video stream based at least in part on the facial recognition data and/or location information (such as landmark data). If images are found in the video stream data, the one or more processors can isolate an associated portion of the video stream data. Moreover, the one or more processors can execute a set of instructions or code to (1) associate contextual data such as time, location, event, etc. with video stream data and (2) define a contextual video stream of the user. The one or more processors can then send, to a client device associated with the user, a signal indicative of an instruction to present the contextual video stream of the user on a display of the client device (e.g., by graphically rendering the contextual video stream in an interface instantiated on the client device).

The system 100 includes a host device 110 in communication with a database 140, a client device 150, and an image capture system 160. The host device 110 can be any suitable host device such as a server or group of servers, a network management device, a personal computer (PC), a processing unit, and/or the like in electronic communication with the database 140, the client device 150, and the image capture system 160. For example, in this embodiment, the host device 110 can be a server or group of servers (disposed in substantially the same location and/or facility or distributed in more than one location) in electronic communication with the database 140, the client device 150, and the image capture system 160 via a network 105, as described in further detail herein.

The client device 150 can be any suitable device such as a PC, a laptop, a convertible laptop, a tablet, a personal digital assistant (PDA), a smartphone, a wearable electronic device (e.g., a smart watch, etc.), and/or the like. Although not shown in FIG. 1, in some embodiments, the client device 150 can be an electronic device that includes at least a memory, a processor, a communication interface, a display, and one or more inputs. The memory, the processor, the communication interface, the display, and the input(s) can be connected and/or electrically coupled to each other such as to allow signals to be sent therebetween. For example, in some embodiments, the memory can be a random access memory (RAM), a memory buffer, a hard drive, a read-only memory (ROM), an erasable programmable read-only memory (EPROM), and/or the like. The processor can be any suitable processing device configured to run or execute a set of instructions or code (e.g., stored in the memory) such as a general-purpose processor (GPP), a central processing unit (CPU), an accelerated processing unit (APU), a graphics processor unit (GPU), an Application Specific Integrated Circuit (ASIC), and/or the like. Such a processor can run or execute a set of instructions or code stored in the memory associated with using a PC application, a mobile application, an internet web browser, a cellular and/or wireless communication (via a network), and/or the like. More specifically, the processor can execute a set of instructions or code stored in the memory associated with sending facial recognition data to and/or receiving facial recognition data and/or contextual video stream data from the host device 110, as described in further detail herein.

The communication interface of the client device 150 can be any suitable module and/or device that can place the resource in communication with the host device 110 such as one or more network interface cards or the like. Such a network interface card can include, for example, an Ethernet port, a WiFi® radio, a Bluetooth® radio, a near field communication (NFC) radio, and/or a cellular radio that can place the client device 150 in communication with the host device 110 via a network (e.g., the network 105) or the like. As such, the communication interface can send signals to and/or receive signals from the processor associated with electronically communicating with the host device 110 via the network 105.

The display of the client device 150 can be, for example, a cathode ray tube (CRT) monitor, a liquid crystal display (LCD) monitor, a light emitting diode (LED) monitor, and/or the like that can graphically represent any suitable portion of the system 100 (e.g., a graphical user interface (GUI) associated with a webpage, PC application, mobile application, and/or the like). In some embodiments, such a display can be and/or can include a touch screen configured to receive a haptic user input. In some instances, the display can be configured to graphically represent data associated with a facial recognition process and/or data associated with a video stream, as described in further detail herein.

The input(s) of the client device 150 can be any suitable module and/or device that can receive one or more inputs (e.g., user inputs) and that can send signals to and/or receive signals from the processor associated with the one or more inputs. In some embodiments, the input(s) can be and/or can include ports, plugs, and/or other interfaces configured to be placed in electronic communication with a device. For example, such an input can be a universal serial bus (USB) port, an Institute of Electrical and Electronics Engineers (IEEE) 1394 (FireWire) port, a Thunderbolt port, a Lightning port, and/or the like. In some embodiments, the display can be included in a touch screen or the like configured to receive a haptic user input.

In some embodiments, an input can be a camera and/or other imaging device. For example, in some embodiments, such a camera can be integrated into the client device 150 (e.g., as in smartphones, tablets, laptops, etc.) and/or can be in communication with the client device 150 via a port or the like (e.g., such as those described above). The camera can be any suitable imaging device such as, for example, a webcam or a forward facing camera included in a smartphone or tablet (e.g., a camera pointed substantially in the same direction as the display). In this manner, the user can manipulate the client device 150 to cause the camera to capture an image (e.g., a photo) or a video. Moreover, in some instances, the display can be configured to graphically render data associated with an image captured by the camera. By way of example, in some embodiments, the client device 150 can be a smartphone, tablet, or wearable electronic device that includes a forward facing camera. In some instances, a user can manipulate the client device 150 to take a picture or video of himself or herself via the camera (e.g., also known as a "selfie").

In some instances, a camera (e.g., an input) included in the client device 150 can be used to capture an image of a user's face, which in turn, can be used to register facial recognition data associated with the user. Specifically, the user can manipulate the client device 150 such that the camera captures an image of the user's face. In some instances, the display can be configured to graphically render an indication, frame, boundary, guide, and/or any other suitable graphical representation of data, which can provide an indication to a user associated with a desired alignment for the image of the user's face. Once the camera captures the desired image, the processor can receive and/or retrieve data associated with the image of the user's face and, in turn, can execute a set of instructions or code (e.g., stored in the memory) associated with at least a portion of a facial recognition process. For example, in some instances, the processor can execute a set of instructions or code associated with verifying an alignment between the indication, frame, boundary, etc. graphically rendered on the display and the captured image of the user's face. In some instances, the client device 150 can be configured to send, via the network 105, a signal associated with data representing the image of the user to the host device 110 when the alignment is verified, and in response, the host device 110 can perform any suitable facial recognition process or processes on the data, as described in further detail herein.

The image capture system 160 can be and/or can include any suitable device or devices configured to capture image data. For example, the image capture system 160 can be and/or can include one or more cameras and/or image recording devices configured to capture an image (e.g., a photo) and/or record a video stream. In some embodiments, the image capture system 160 can include multiple cameras in communication with a central computing device such as a server, a personal computer, a data storage device (e.g., a network attached storage (NAS) device, a database, etc.), and/or the like. In such embodiments, the cameras can be autonomous (e.g., can capture image data without user prompting and/or input), and can each send image data to the central computing device (e.g., via a wired or wireless connection, a port, a serial bus, a network, and/or the like), which in turn, can store the image data in a memory and/or other data storage device. Moreover, the central computing device can be in communication with the host device 110

(e.g., via the network 105) and can be configured to send at least a portion of the image data to the host device 110. Although shown in FIG. 1 as being in communication with the host device 110 via the network 105, in other embodiments, such a central computing device can be included in, a part of, and/or otherwise coupled to the host device 110. In still other embodiments, the cameras can be in communication with the host device 110 (e.g., via the network 105) without such a central computing device.

In some embodiments, the image capture system 160 can be associated with and/or owned by a venue or the like such as, for example, a sports arena, a theme park, a theater, and/or any other suitable venue. In other embodiments, the image capture system 160 can be used in or at a venue but owned by a different entity (e.g., an entity licensed and/or otherwise authorized to use the image capture system 160 in or at the venue such as, for example, a television camera at a sporting event). In still other embodiments, the image capture system 160 can include any number of client devices (e.g., user devices) or the like such as smartphones, tablets, etc., which can be used as cameras or recorders. In such embodiments, at least some of the client devices can be in communication with the host device 110 and/or a central computing device associated with the venue (e.g., as described above).

For example, in some embodiments, the camera integrated into the client device 150 can form and/or comprise at least a portion of the image capture system 160, as shown in FIG. 1B. In this manner, the user can manipulate the client device 150 to capture a picture and/or video recording and in response, the client device 150 can upload and/or otherwise send the picture (e.g., image data, photographic data, etc.) and/or video recording data to the host device 110. In some instances, the picture and/or video recording data can be stored on the client device 150 for any suitable time and uploaded and/or sent to the host device 110 at a later time. Moreover, the picture and/or video recording data can be stored on the client device 150 after the picture and/or video recording data is sent to the host device 110. That is to say, sending the picture and/or video recording data does not delete and/or remove the picture and/or video recording data from the client device 150 (e.g., a copy of the data is sent to the host device 110). Thus, as shown in FIG. 1B, the image capture system 160 need not be associated with a particular event and/or venue. In such instances, the user can manipulate the client device 150 (e.g., an application of the client device 150) to capture user generated content (e.g., pictures, image data, photographic data, video stream data, etc.) via the camera and/or recording device (e.g., the image capture system 160) integrated into the client device 150.

In some instances, the image capture system 160 is configured to capture image data associated with a venue and/or event. In other words, the image capture system 160 is configured to capture image data within a predetermined, known, and/or given context. For example, in some instances, the image capture system 160 can include one or more image capture devices (e.g., cameras and/or video recorders) that are installed at an arena or the like and that are configured to capture image data associated with patrons, guests, performers, etc. at the arena. In this manner, the image capture system 160 is configured to capture image data within the context of the arena and/or an event occurring at the arena. Thus, the captured image data can be, for example, "contextual image data." That is to say, the image data is associated with contextual data. As described in further detail herein, the host device 110 can receive the image data and/or video stream data from the image capture system 160 and data associated with the context (e.g., "contextual data" associated with the arena and/or the event occurring at the arena, and/or any other suitable contextual and/or metadata) from any suitable data source and/or the like; can associate the contextual data with, for example, the image data; can define a user-specific contextual image and/or user-specific contextual video stream associated with, for example, a user of the client device 150; and can send the user-specific contextual image and/or user-specific contextual video stream associated with the user to the client device 150.

As described above, the client device 150 and the image capture system 160 can be in communication with the host device 110 via one or more networks. For example, as shown in FIG. 1A, the client device 150 and the image capture system 160 can be in communication with the host device 110 via its communication interface and the network 105. The network 105 can be any type of network such as, for example, a local area network (LAN), a virtual network such as a virtual local area network (VLAN), a wide area network (WAN), a metropolitan area network (MAN), a worldwide interoperability for microwave access network (WiMAX), a cellular network, the Internet, and/or any other suitable network implemented as a wired and/or wireless network. By way of example, the network 105 can be implemented as a wireless local area network (WLAN) based on the Institute of Electrical and Electronics Engineers (IEEE) 802.11 standards (also known as "WiFi®"). Moreover, the network 105 can include a combination of networks of any type such as, for example, a LAN or WLAN and the Internet. In some embodiments, the client device 150 can communicate with the host device 110 and the network 105 via intermediate networks and/or alternate networks (not shown), which can be a similar to or different from the network 105. As such, the client device 150 can send data to and/or receive data from the host device 110 using multiple communication modes (e.g., associated with any of the networks described above) that may or may not be transmitted to the host device 110 using a common network. For example, the client device 150 can be a mobile telephone (e.g., smartphone) connected to the host device 110 via a cellular network and the Internet (e.g., the network 105).

In some instances, the network can facilitate, for example, a peer networking session or the like. In such instances, the peer networking session can include, for example, client devices and/or any other suitable electronic device, each of which share a common characteristic. For example, in some instances, the peer networking session can include any suitable client device (e.g., an electronic device registered in the database 140 and/or the like) that is within a predetermined proximity of a venue, event, location, etc. For example, in some instances, such a peer networking session can include any number of registered client devices present at a venue (e.g., a sports event). In some instances, the peer networking session can be automatically established based on contextual data associated with the user and/or the client device. In other instances, the peer networking session can be automatically established based on one or more users "checking-in" and/or otherwise publicizing his or her presence at the venue or the like (e.g., "squawk" the user's presence). In some instances, a user can "check-in" at a time the user arrived at an event or the like (e.g., sports event, concert, wedding, birthday party, gathering, etc.), at a time of registration, at a time of capturing an image or video stream, and/or the like. Further, the "check-in" can include identifying information such as, for example, geo-location data, date and time data, personal or user identification data, etc. In some implementations, a user can also, via an application on their client device 150, search for events and/or locations for which contextual video stream data has been captured. The user can "check-in" to the event and/or locations that are returned from the search. As described herein, checking into an event and/or location can initiate processing of the contextual video stream data associated with that event and/or location, e.g., to determine whether or not the user can be matched to the contextual video stream data.

In other instances, a user can manually establish a peer networking session including, for example, a predetermined set or group of users. In some instances, such peer networking sessions can be public networks, private networks, and/or otherwise limited access networks. For example, in some instances, a user can request to join a networking session and/or can receive an invite to join a networking session and/or the like. In some instances, establishing a peer networking session can, for example, facilitate communication (e.g., group chat sessions or the like) and/or sharing of image and/or video data between users included in the peer networking session.

The host device 110 can be any suitable device configured to send data to and/or receive data from the database 140, the client device 150, and/or the image capture system 160. In some embodiments, the host device 110 can function as, for example, a server device (e.g., a web server device), a network management device, an administrator device, and/or so forth. In some embodiments, the host device 110 can be a group of servers or devices housed together in or on the same blade, rack, and/or facility or distributed in or on multiple blades, racks, and/or facilities. The host device 110 includes at least a memory 115, a processor 120, and a communication interface 125 (see e.g., FIG. 2). In some embodiments, the memory 115, the processor 120, and the communication interface 125 are connected and/or electrically coupled so that signals can be sent between the memory 115, the processor 120, and the communication interface 125. The host device 110 can also include and/or can otherwise be operably coupled to the database 140 configured to store user data, facial recognition data, contextual data (e.g., associated with a time, location, venue, event, etc.), video streams, and/or the like.

The memory 115 can be, for example, RAM, a memory buffer, a hard drive, a database, a ROM, an EPROM, an EEPROM, and/or so forth. In some instances, the memory 115 of the host device 110 includes a set of instructions or code used to perform one or more facial recognition actions and/or used to communicate (e.g., send and/or receive) data with at least one device (e.g., the client device 150) using one or more suitable communication modes. The processor 120 can be any suitable processor such as, for example, a GPP, a CPU, an APU, a GPU, a network processor, a front-end processor, an ASIC, an FPGA, and/or the like. Thus, the processor 120 can be configured to perform and/or execute a set of instructions, modules, and/or code stored in the memory 115. For example, the processor 120 can be configured to execute a set of instructions and/or modules associated with, inter alia, receiving facial recognition data (e.g., from the client device 150), analyzing the facial recognition data, registering and/or storing the facial recognition data, receiving video stream data (e.g., from the image capture system 160), analyzing the video stream data and comparing the video stream data to the facial recognition data, sending video stream data (e.g., to the client device 150), receiving and/or analyzing characteristics of the video stream data (e.g., location information determined based on such as background landmark and/or background scenery data included in the video stream data, and/or the like), and/or any other suitable process, as further described herein. The communication interface 125 can be any suitable device that can place the host device 110 in communication with the database 140, the client device 150, the image capture device 160 and/or any other suitable device and/or service in communication with the network 105 (e.g., any device configured to gather and/or at least temporarily store data such as facial recognition data, video streams, and/or the like). In some embodiments, the communication interface 125 can include one or more wired and/or wireless interfaces, such as, for example, network interface cards (NIC), Ethernet interfaces, optical carrier (OC) interfaces, asynchronous transfer mode (ATM) interfaces, and/or wireless interfaces (e.g., a WiFi® radio, a Bluetooth® radio, an NFC radio, and/or the like).

Returning to FIG. 1A, the database 140 associated with the host device 110 can be any suitable database such as, for example, a relational database, an object database, an object-relational database, a hierarchical database, a network database, an entity-relationship database, a structured query language (SQL) database, an extensible markup language (XML) database, digital repository, a media library, a cloud server or storage, and/or the like. In some embodiments, the host device 110 can be in communication with the database 140 over any suitable network (e.g., the network 105) via the communication interface 125. In such embodiments, the database 140 can be included in or stored by a network attached storage (NAS) device that can communicate with the host device 110 over the network 105 and/or any other network(s). In other embodiments, the database can be stored in the memory 115 of the host device 110. In still other embodiments, the database can be operably coupled to the host device 110 via a cable, a bus, a server rack, and/or the like.

The database 140 can store and/or at least temporarily retain data associated with the video recognition system 100. For example, in some instances, the database 140 can store data associated with and/or otherwise representing user profiles, resource lists, facial recognition data, modes, and/or methods, contextual data (e.g., associated with a time, location, venue, event, etc.), video streams or portions thereof, location information (such as landmark data), and/or the like. In other words, the database 140 can store data associated with users whose facial image data has be registered by the system 100 (e.g., "registered users"). In some embodiments, the database 140 can be and/or can include a relational database, in which data can be stored, for example, in tables, matrices, vectors, etc. according to the relational model. By way of example, in some instances, the host device 110 can be configured to store in the database 140 video stream data received from a video or image source (e.g., the image capture system 160) and contextual data associated with the video stream data. In some instances, the video stream data and the contextual data associated therewith can collectively define a contextual video stream or the like, as described in further detail herein. In other instances, the video stream data can be stored in the database 140 without contextual data or the like.

In some implementations, the user profiles can be user profile data structures that include information relating to users accessing video stream data. For example, a user profile data structure can include a user profile identifier, facial recognition data (e.g., data obtained from an image of the user (e.g., facial characteristic data) that can be used to match the user to an image from the contextual video stream data), a list of identifiers associated with contextual video stream data structures stored in the database 140 and associated with the user, a list of identifiers associated with the user profile data structures of other users with which the user is associated (e.g., as a friend and/or contact), user location data, and/or the like.

In some implementations, users can add each other as friends within an application through which they access contextual video stream data. Users can also be automatically be associated with each other, e.g., when a user associated with a first user profile is a contact of another user associated with a second user profile. For example, a user operating a client device can have a list of contacts, and/or other contact information, stored at the client device. The application can retrieve and import the contact information, can match the contact information to information in at least one user profile in the database, and can automatically associate that at least one user profile with that user. In some implementations, the users can be associated with each other by storing a list of friends and/or contacts (e.g., a list of identifiers of user profiles to be added as friends of a particular user) within each user profile of each user. When a user adds a friend and/or contact, the user can automatically be notified when the friend and/or contact records and/or receives contextual video stream data, and/or the like. In some implementations, the host device 110 can also use the stored relationships between users to automatically process contextual video stream data associated with the user (e.g., to determine whether friends and/or contacts of the user can be found within the contextual video stream data). For example, when the contextual video stream data is received, when a friend and/or contact is associated with the user, and/or the like, the host device 110 can automatically process the contextual video stream data to determine whether facial image data associated with the friends and/or contacts of the user can be matched to the contextual video stream data.

Although the host device 110 is shown and described with reference to FIG. 1 as including and/or otherwise being operably coupled to the database 140 (e.g., a single database), in some embodiments, the host device 110 can be operably coupled to any number of databases. Such databases can be configured to store at least a portion of a data set associated with the system 100. For example, in some embodiments, the host device 110 can be operably coupled to and/or otherwise in communication with a first database configured to receive and at least temporarily store user data, user profiles, and/or the like and a second database configured to receive and at least temporarily store video stream data and contextual data associated with the video stream data. In some embodiments, the host device 110 can be operably coupled to and/or otherwise in communication with a database that is stored in or on the client device 150 and/or the image capture system 160. In other words, at least a portion of a database can be implemented in and/or stored by the client device 150 and/or the image capture system 160. In this manner, the host device 110 and, in some instances, the database 140 can be in communication with any number of databases that can be physically disposed in a different location than the host device 110, while being in communication with the host device 110 (e.g., via the network 105).

In some embodiments, the database 140 can be a searchable database and/or repository. For example, in some instances, the database 140 can store video stream data associated with a user (e.g., contextual video stream data). In some instances, the user can search the database 140 to retrieve and/or view one or more contextual video streams associated with the user that are stored in the database 140. In some instances, the user can have a limited access and/or privileges to update, edit, delete, and/or add video streams associated with his or her user profile (e.g., user-specific contextual video streams and/or the like). In some instances, the user can, for example, update and/or modify permissions and/or access associated with the user-specific video streams associated with that user. For example, in some instances, the user can redistribute, share, and/or save data associated with the user. In other instances, the user can block access to user-specific data and/or the like. In some instances, the user can redistribute and/or share content, data, and/or video streams otherwise shared with the user (e.g., that may or may not be associated with the user).

Figure 2:
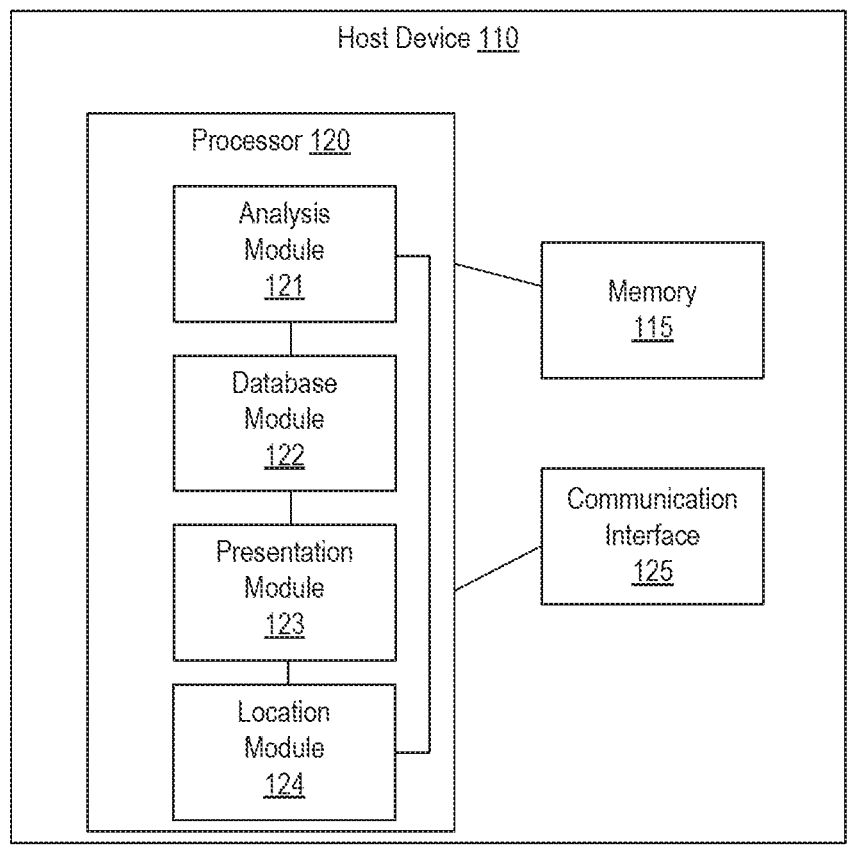
FIG. 2 is a schematic illustration of a host device included in the recognition system of FIG. 1.

Returning to FIG. 2, as described above, the processor 120 of the host device 110 can be configured to execute specific modules. The modules can be, for example, hardware modules, software modules stored in the memory 115 and/or executed in the processor 120, and/or any combination thereof. For example, as shown in FIG. 2, the processor 120 includes and/or executes an analysis module 121, a database module 122, a presentation module 123, and a location module 124. As shown in FIG. 2, the analysis module 121, the database module 122, the presentation module 123, and the location module can be connected and/or electrically coupled. As such, signals can be sent between the analysis module 121, the database module 122, the presentation module 123, and the location module 124.

The analysis module 121 includes a set of instructions that can be executed by the processor 120 (or portion thereof) that are associated with receiving and/or collecting data associated with a facial recognition of a user and/or a video stream. More particularly, the analysis module 121 can be operably coupled to and/or otherwise in communication with the communication interface 125 and can receive data therefrom. Such data can be, for example, associated with a user (e.g., facial recognition information, profile information, preferences, activity logs, location information, contact information, calendar information, social media activity information, etc.), a venue (e.g., location data, resource data, event schedule), an event, and/or the like. As described in further detail herein, the analysis module 121 can receive a signal from the communication interface 125 associated with a request and/or an instruction to perform and/or execute any number of processes associated with facial recognition.

In some instances, the analysis module 121 can receive data from the communication interface 125 at substantially real-time. That is to say, in some instances, an electronic device included in the system 100 (e.g., the client device 150) can be manipulated by a user to define and/or update data associated with facial recognition of the user and once defined and/or updated can send the data to the host device 110 via the network 105. Thus, the communication interface 125 can, upon receiving the data, send a signal to the analysis module 121, which receives the data in a very short time period after being defined and/or updated by the electronic device. In other embodiments, the analysis module 121 can receive data from the communication interface 125 at a predetermined rate or the like based on, for example, an aggregation process, a current and/or predicted processor, memory, and/or network load, and/or the like.

As described above, the analysis module 121 can be configured to receive, aggregate, analyze, sort, parse, alter, and/or update data associated with a facial recognition process or the like. More particularly, in some instances, a user can manipulate the client device 150 to capture one or more images or video streams of his or her face (as described in further detail herein) and, in turn, can send signals associated with and/or representing the image data to the host device 110, for example, via the network 105. In some instances, the communication interface 125 can receive the image data and can send an associated signal to the analysis module 121. Upon receipt, the analysis module 121 can execute a set of instructions or code (e.g., stored in the analysis module 121 and/or in the memory 115) associated with aggregating, analyzing, sorting, updating, parsing, and/or otherwise processing the image data. More specifically, the analysis module 121 can perform any suitable facial recognition process and/or algorithm such as, for example, Principal Component Analysis using Eigenfaces (e.g., Eigenvector associated with facial recognition), Linear Discriminate Analysis, Elastic Bunch Graph Matching using the Fisherface algorithm, Hidden Markov model, Multilinear Subspace Learning using tensor representation, neuronal motivated dynamic link matching, convolutional neural nets (CNN), and/or the like or combination thereof. In some implementations, image data the user provides to the host device 110 can be used in subsequent facial recognition processes to identify the user, via the analysis module 121.

The analysis module 121 can define a user profile or the like that includes the user's image data, and any other suitable information or data associated with the user such as, for example, a picture, video recording and/or audio recording, personal and/or identifying information (e.g., name, age, sex, birthday, hobbies, etc.), calendar information, contact information (e.g., associated with the user and/or the user's friends, family, associates, etc.), device information (e.g., a media access control (MAC) address, Internet Protocol (IP) address, etc.), location information (e.g., current location data and/or historical location data), social media information (e.g., profile information, user name, password, friends or contacts lists, etc.), and/or any other suitable information or data. As such, the analysis module 121 can send a signal to the database module 122 indicative of an instruction to store the user profile data in the database 140, as described in further detail herein.

In some instances, the analysis module 121 can receive video stream data (or image data, for example, from a photograph) and can be configured to analyze and/or process the video stream data to determine if a portion of the video stream data matches any suitable portion of users' image data. That is to say, the analysis module 121 can use previously-stored user image data as a template against which data included in the video stream is compared. Said another way, the analysis module 121 performs a facial recognition process and/or analysis on the video stream data based at least in part on the previously-stored user image data. In some embodiments, the host device 110 and more particularly, the communication interface 125 receives the video stream data from the image capture system 160 either directly (e.g., from one or more cameras via the network 105) or indirectly (e.g., from a computing device via the network 105, which in turn, is in communication with the one or more cameras). In some embodiments, the analysis module 121 can be configured to analyze and/or process the video stream data based at least in part on separating, parsing, sorting, and/or otherwise deconstructing the video stream data into its individual frames (e.g., a static image at a predetermined time during the video stream). As such, the analysis module 121 can compare and/or analyze data included in the video stream frame relative to the previously-stored user image data.

In some instances, the analysis module 121 can also analyze the video stream data to determine contextual information associated with the video stream such as, for example, location, venue, time, coinciding event (e.g., a sports team scoring a goal, being captured, for example, on a "kiss cam," etc.), and/or any other suitable contextual information. In some instances, the analysis module 121 can be configured to match, aggregate, and/or otherwise associate at least a portion of the video stream to the contextual data. For example, in some instances, the video stream data can represent, for example, a user at a sporting event. In such instances, the contextual data can be, for example, a video stream of the sporting event or game, and can include data associated with a time, location, venue, teams, etc. As such, the analysis module 121 can be configured to aggregate the video stream data and the contextual data such that the video stream data and the contextual data substantially coincide (e.g., occur and/or capture data associated with substantially the same time). In other instances, the contextual data can include data associated with any other suitable context. In some instances, the analysis module 121 can be configured to use the contextual information associated with the video stream, along with data relating to the location of a user, to further connect the video stream to a particular user. The analysis module 121 can be configured to compare the contextual information to a user's location prior to comparing data included in the video stream to the previously-stored user image data (see FIGS. 5 and 6 for more details).

If the analysis module 121 determines that at least a portion of the data in the video stream satisfies a criterion (e.g., matches the previously-stored user image data to a predetermined and/or acceptable probability), the analysis module 121 can send one or more signals to the database module 122 indicative of an instruction to store at least the portion of the image and/or video stream data in the database 140 and to associate and/or otherwise store that data with the previously-stored user image data. In some instances, the analysis module 121 can send signals to the database module 122 such that individual frames are stored in the database 140, which in turn, can be subsequently retrieved and processed to define a video stream. In other instances, the analysis module 121 can send one or more signals to the database module 122 such that the portion of the video stream data is stored in the database 140. That is to say, the analysis module 121 can at least partially redefine and/or reconstruct the video stream from the individual frames (that were separated or deconstructed as described above).

In some instances, the host device 110 can receive video stream data (e.g., from the image capture system 160 and via the network 105 and the communication interface 125) and the analysis module 121 and/or any other suitable module not shown in FIG. 2, can perform one or more pre-processing and/or pre-sorting procedures prior to performing the facial recognition process (just described). For example, in some embodiments, the analysis module 121 (or other module) can analyze the video stream data to determine and/or define a data set including, for example, identifying information and/or contextual information such as location, time, event, etc. Once defined, the analysis module 121 can analyze user data stored in the database 140 (e.g., via sending a signal to the database module 122 indicative of an instruction to query the database 140 and/or the like) to determine if a portion of data associated with a user satisfies a criteria(ion) such as matching the data set including the contextual information associated with the video stream.

In some instances, the criteria(ion) can be associated with a confidence level and/or matching threshold, represented in any suitable manner (e.g., a value such as a decimal, a percentage, and/or the like). For example, in some instances, the criteria(ion) can be a threshold value or the like such as a 70% match of the video stream data and at least a portion of the data stored in the database, a 75% match of the video stream data and at least a portion of the data stored in the database, a 80% match of the video stream data and at least a portion of the data stored in the database, a 85% match of the video stream data and at least a portion of the data stored in the database, a 90% match of the video stream data and at least a portion of the data stored in the database, a 95% match of the video stream data and at least a portion of the data stored in the database, a 97.5% match of the video stream data and at least a portion of the data stored in the database, a 99% match of the video stream data and at least a portion of the data stored in the database, or any percentage therebetween.

In some instances, the data associated with the user can include, for example, calendar data, location data, preference data, and/or the like. If, for example, the data does not satisfy the criterion, the analysis module 121 can define an indication that the data associated with that user can be excluded from, for example, the facial recognition process. In this manner, the pre-processing and/or pre-sorting can reduce an amount of processing load or the like during the facial recognition process. Although described above as querying the database 140 for the user data, in some embodiments, the host device 110 can send a signal to a device associated with the user (e.g., the client device 150) indicative of a request for location data or the like associated with that device. Upon receipt of the location data (e.g., global positioning service (GPS) data of the device, using location information and/or characteristics, such as landmark and/or background scenery, within an image or video, etc.) or the like, the analysis module 121 can determine if the location data matches the location data associated with the video stream, as described above.

By way of example, in some instances, analysis module 121 can receive video stream data from a sporting event that also includes location data associated with, for example, an arena. In response, the analysis module 121 can send a request for location data from a client device (e.g., the client device 150) associated with a user. If, for example, the location data associated with the video stream and the location data associated with the client device are substantially similar (e.g., the location data associated with the video stream and the location data associated with the client device indicate that the source of the video stream and the client device are and/or were within a predetermined distance of each other) and/or the location data associated with the client device is within a predetermined range of location data values or the like, the analysis module 121 can increase a confidence score and/or otherwise consider the result as contributing to meeting the threshold and/or otherwise satisfying the criteria(ion). The location data can be, for example, geo-location data based on a GPS, network location and/or data (e.g., via NFC verification, Bluetooth verification, cellular triangulation, cognitive network switching and/or protocols, etc.), social network data such as a "check-in", and/or the like. For example, the location module 124 can process the location data so as to identify the location of the video stream and/or the user, and to provide data to the analysis module 121 so as to allow the analysis module 121 to modify the confidence score. In this manner, the confidence score can be calculated based on the location data.

In other implementations, the location module 124 can process the location data and can provide the processed location data to the analysis module 121 when location data associated with the video stream and location data associated with the user are substantially similar (e.g., the location data associated with the video stream and the location data associated with the client device indicate that the source of the video stream and the client device are and/or were within a predetermined distance of each other). The analysis module 121 can then generate and/or modify a confidence score based on the location data and a facial recognition analysis of the video stream. In this manner, the confidence score may be generated and/or modified when the location data associated with the video stream and location data associated with the user are determined to be substantially similar and may not be generated and/or modified when the location data associated with the video stream and location data associated with the user are not substantially similar. Further, in this manner, the confidence score can be calculated as a result of both a location data analysis and a facial recognition analysis. More details on the location module 124 can be found at least in FIGS. 5-6. In this manner, the host device 110 (e.g., via the analysis module 121) can determine, for example, a proximity of a client device to a location where the video stream data was captured.

Although described as analyzing location data, in other instances, the analysis module 121 can analyze data associated with any suitable source, activity, location, pattern, purchase, etc. For example, in some instances, the analysis module 121 can analyze ticket sales associated with a venue. In other instances, the analysis module 121 can analyze social media posts, comments, likes, etc. In some instances, the analysis module 121 can collect and/or analyze data associated with a user (as described above) and can define, for example, a user profile that can include, inter alia, user identification data, facial recognition data, client device data, purchase data, internet web browsing data, location data, social media data, preference data, etc. Thus, a user's profile data can be analyzed to determine a confidence score, value, and/or indicator, which can be evaluated relative to a threshold score, value, and/or indicator to determine if the user data and/or the video stream data satisfy the criteria (ion). Accordingly, in such embodiments, non-facial recognition data (e.g., ticket sales data, social media posts, and/or characteristics such as a wardrobe of an individual in a video or image, location data such as landmarks within the image, background scenery data, etc.) can be used to corroborate the facial recognition data and/or increase/decrease a confidence score.

Although the analysis module 121 is described above as analyzing the video stream data to define facial recognition data and contextual data associated with the video stream, in other embodiments, the facial recognition process and the contextual data process can be performed separately and/or independently. For example, in some embodiments, the analysis module 121 can be configured to perform the facial recognition process while a different module, processor, device, server, etc. can be configured to perform the contextual data process. For example, the location module 124 can perform analysis of the image and/or video stream based on location data, characteristics of the image, and/or the like. Thus, a time to analyze the video stream data can be reduced and/or the processing load can be distributed when compared to the facial recognition process and the contextual data process being performed by the same module.

As described above, the database module 122 includes a set of instructions executed by the processor 120 (or portion thereof) that is associated with monitoring the database 140 and/or updating data stored therein. For example, the database module 122 can include instructions to cause the processor 120 to update data stored in the database 140 with at least a portion of the facial recognition data received from the analysis module 121. More specifically, the database module 122 can receive, for example, the user image data associated with the user from the analysis module 121 and, in response, can store the user image data in the database 140. In some instances, the database module 122 can receive a signal from the analysis module 121 indicative of a request to query the database 140 to determine if the data stored in the database 140 and associated with the user image data for the user matches any suitable portion of the video stream data, as described above. If, for example, at least a portion of the video stream data satisfies a criteria(ion) (referred to henceforth as "criterion" for simplicity and not to the exclusion of multiple "criteria"), the database module 122 can be configured to update the data stored in the database 140 associated with that user. That is to say, if at least a portion of the video stream data matches the user image data within a predetermined probability or the like. If, however, the video stream data does not match the user image data stored in the database 140, the database module 122 can, for example, query the database 140 for the next entry (e.g., data associated with the next user) and/or can otherwise not update the database 140. Moreover, the database module 122 can be configured to store the data in the database 140 in a relational-based manner (e.g., the database 140 can be a relational database and/or the like) and/or in any other suitable manner.

The presentation module 123 includes a set of instructions executed by the processor (or a portion thereof) that is associated with defining a contextual video stream and/or presentation representing at least a portion of the video stream data satisfying the criterion during the facial recognition process, as described above. More specifically, the presentation module 123 can be configured to define a contextual video stream and/or presentation representing an identified user (e.g., via facial recognition) at an event, venue, location, and/or the like. Once the contextual video stream is defined, the presentation module 123 can send a signal associated with the contextual video stream to the communication interface 125, which in turn, can send a signal (e.g., via the network 105) to the client device 150 that is indicative of an instruction to graphically render the contextual video stream on its display.

Although the presentation module 123 and/or other portion of the host device 110 is described above as sending a signal to the client device 150 indicative of an instruction to present the contextual video stream on the display of the client device 150, in other instances, the presentation module 123 can define the contextual video stream and can send a signal to the database module 122 indicative of an instruction to store the contextual video stream in the database 140. In such instances, the data associated with the contextual video stream can be stored and/or otherwise associated with the user data stored in the database 140. In some instances, the host device 110 can retrieve the contextual video stream from the database 140 in response to a request from the client device 150 (and/or any other suitable device). More specifically, in some embodiments, the user can manipulate the client device 150 to access a webpage on the Internet. After being authenticated (e.g., entering credentials or the like) the user can interact with the webpage such that a request for access to the contextual video stream is sent from the client device 150 to the host device 110. Thus, the host device 110 (e.g., the database module 122) can retrieve the contextual video stream from the database 140 and can send a signal to the client device 150 operable in presenting the contextual video stream on the display (e.g., by rendering the contextual video stream via the Internet and the webpage). In other words, the contextual video stream can be stored on the "cloud" and accessed via a web browser and the Internet.

Although the analysis module 121, the database module 122, and the presentation module 123 are described above as being stored and/or executed in the host device 110, in other embodiments, any of the modules can be stored and/or executed in, for example, the client device 150 and/or the image capture system 160. For example, in some embodiments, the client device 150 can include, define, and/or store a presentation module (e.g., as a native application). The presentation module can be substantially similar to or the same as the presentation module 123 of the host device 110. In such embodiments, the presentation module of the client device 150 can replace the function of the presentation module 123 otherwise included and/or executed in the host device 110. Thus, the presentation module of the client device 150 can receive, for example, a data set associated with a contextual video stream and upon receipt, can define a presentation to be presented on the display of the client device 150.

Figure 3:
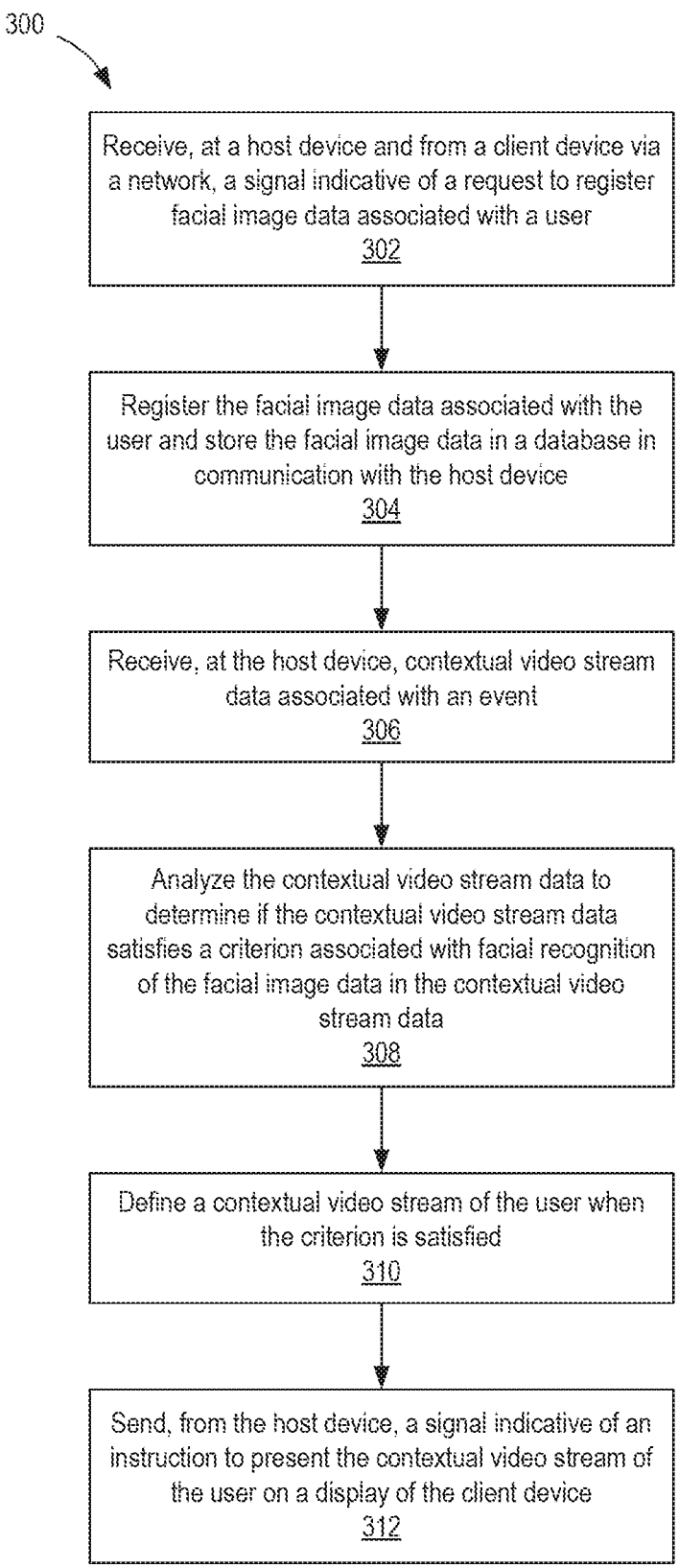
FIG. 3 is a flowchart illustrating a method of using a video recognition system according to an embodiment.

FIG. 3 is a flowchart illustrating a method 300 of defining a contextual video stream according to an embodiment. The method 300 includes receiving, at a host device and from a client device via a network, a signal indicative of a request to register facial image data associated with a user, at 302. For example, in some embodiments, the network can be any suitable network or combination of networks such as, for example, the network 105 described above with reference to FIG. 1. The host device can be substantially similar to or the same as the host device 110 described above with reference to FIGS. 1 and 2. Similarly, the client device can be substantially similar to or the same as the client device 150 described above with reference to FIGS. 1-2. In some instances, the client device can be configured to capture initial facial image data and can send the initial facial image data to the host device. Specifically, in some embodiments, the client device can be configured to capture a user's facial image or images in any suitable manner. Accordingly, the host device can receive facial image data from the client device and can perform any suitable process or the like associated with registering a user and/or the user's facial image data.

The method 300 includes registering the facial recognition data associated with the user and storing the facial recognition data in a database in communication with the host device, at 304. The database can be any suitable database such as, for example, the database 140 described above with reference to FIG. 1. The registering of the facial recognition data can include any suitable process, method, and/or algorithm associated with facial recognition such as those described above. In some instances, the host device can be configured to define user image data or the like based on the facial recognition and can store at least a portion of the user image data in the database.

The host device receives contextual video stream data associated with an event and/or location, at 306. The host device can receive the contextual video stream data from an image capture system such as the image capture system 160 (e.g., a camera and/or client device) described above with reference to FIG. 1. More specifically, the host device can receive the contextual video stream data either directly (e.g., from one or more cameras via the network) or indirectly (e.g., from a computing device via the network, which in turn, is in communication with the one or more cameras).

In one example, a camera can record the contextual video stream data, and can send the contextual video stream data to the host device. In another example, a user can record video through an application running on a client device being operated by the user (e.g., via a User-Generated Content (UGC) interface within the application running on the client device). By initiating recording through the application (e.g., by clicking a "Record" and/or similar button in the UGC interface), the user can record a contextual video stream, with which the client device can associate location data (e.g., geolocation, data from Near Field Communication (NFC), data from Bluetooth communications with other devices, cellular triangulation, event and/or location check-in data, and/or network Wi-Fi connection information) with the contextual video stream. Specifically, the contextual video stream can be tagged with the location data, and/or can be associated with a data structure encapsulating the location data.

The contextual video stream data is analyzed to determine if the contextual video stream data satisfies a criterion associated with facial recognition of the facial image data in the contextual video stream data, at 308. For example, the host device can receive the contextual video stream data (or image data, for example, from a photograph) and can analyze and/or process the contextual video stream data to determine if a portion of the contextual video stream data matches any suitable portion of the facial image data. That is to say, the host device can use the facial image data as a template against which data included in the contextual video stream is compared. Said another way, the host device performs a facial recognition process and/or analysis on the contextual video stream data based at least in part on the facial image data. In some instances, the criterion can be, for example, associated with a matching of the contextual video stream data with the facial image data with a predetermined and/or acceptable probability. In some embodiments, the host device can be configured to analyze and/or process the contextual video stream data based at least in part on separating, parsing, sorting, and/or otherwise deconstructing the contextual video stream data into its individual frames (e.g., a static image at a predetermined time during the video stream). As such, the host device can compare and/or analyze data included in the contextual video stream frame relative to the facial image data.

In some instances, the analysis of the contextual video stream data also includes analyzing the contextual video stream data to determine contextual information associated with the video stream such as, for example, location, venue, time, coinciding event (e.g., a sports team scoring a goal, being captured, for example, on a "kiss cam," etc.), landmarks within the image, and/or any other suitable contextual information. In some instances, the host device can be configured to match, aggregate, and/or otherwise associate at least a portion of the video stream to the contextual data. For example, in some instances, the video stream data can represent, for example, a user at a sporting event. In such instances, the contextual data can be, for example, a video stream of the sporting event or game, and can include data associated with a time, location, venue, teams, etc. As such, the host device can be configured to aggregate the video stream data and the contextual data such that the video stream data and the contextual data substantially coincide (e.g., occur and/or capture data associated with substantially the same time). In other instances, the contextual data can include data associated with any other suitable context.

A contextual video stream of the user is defined when the criterion associated with facial recognition of the facial image data in the contextual video stream data is satisfied, at 310. For example, when the host device determines that at least a portion of the data in the contextual video stream satisfies a criterion (e.g., matches the facial image data to a predetermined and/or acceptable probability), the host device can define the contextual video stream of the user and can store the contextual video stream of the user in the database. With the contextual video stream of the user defined, the host device sends a signal indicative of an instruction to present the contextual video stream of the user on a display of the client device, at 312 (e.g., by graphically rendering the contextual video stream in an interface instantiated on the client device). For example, in some embodiments, the host device can send a signal to the client device, via the network, that is operable in presenting the contextual video stream of the user on the display of the client device. In other embodiments, the host device can store the contextual video stream (e.g., in the database or the like) and can be configured to retrieve the contextual video stream of the user from the database in response to a request from the client device (and/or any other suitable device). More specifically, in some embodiments, the user can manipulate the client device to access a webpage on the Internet. After being authenticated (e.g., entering credentials or the like) the user can interact with the webpage such that a request for access to the contextual video stream is sent from the client device to the host device. Thus, the host device can retrieve the contextual video stream from the database and can send a signal to the client device operable in presenting the contextual video stream on the display (e.g., by graphically rendering the contextual video stream via the Internet and the webpage). In other words, the contextual video stream can be stored on the "cloud" and accessed via a web browser and the Internet.

In other implementations, when a contextual video stream satisfies the criterion (e.g., when the contextual video stream matches the facial image data of the user to a predetermined probability, and/or the like), the host device can automatically send the contextual video stream data to the user. For example, in some implementations, the user may also be operating a client device instantiating an application that is tracking user location data for that user. When an image capture device (e.g., such as an autonomous camera and/or another user) records contextual video stream data, the host device can determine that the contextual video stream data matches the user based on a facial analysis of the contextual video stream and facial image data associated with the user. The user's client device can also send location data associated with the user and the client device to the host device. The host device can refine, using both the facial analysis and the location information, the probability that the user appears in the contextual video stream. If the probability that the user appears in the contextual video stream satisfies a criterion (e.g., exceeds a predetermined threshold, and/or the like), the host device can send the contextual video stream data to the user. Alternatively, the host device can pre-filter the contextual video stream based on the location information, such that the probability is calculated when location information of the user is substantially similar to location information of the contextual video stream, and does not calculate the probability when the location data of the contextual video stream is not substantially similar to the location information of the user.

In other implementations, when a contextual video stream satisfies the criterion (e.g., when the contextual video stream matches the facial image data of the user to a predetermined probability, and/or the like), the host device can store the contextual video stream data and associate the contextual video stream data with the user based on the user's interaction with the video. For example, in some implementations, the user can access an application instantiated on a client device associated with the user, to search for and/or access the contextual video stream data. The user can, for example, view the contextual video stream data within the user profile of another user associated with that user, and/or can search for contextual video stream data to view within an interface of the application. When the user accesses the contextual video stream data within the application, the application can send a signal to the host device indicating that the user is accessing that contextual video stream data. The host device can automatically determine whether or not a facial analysis of the contextual video stream data has been performed based on the facial image data associated with that user, and can automatically perform a facial analysis of the contextual video stream data, based on that user's facial image data, if the user's facial image data has not been previously compared to the contextual video stream data. In this manner, the host device can delay processing the contextual video stream data to identify users within the contextual video stream data, until users attempt to access the contextual video stream data.

In some instances, a user can search for an event and "check-in" to that event after the event. For example, the user can identify an event (e.g., by viewing a list of events, by viewing location of events on a map, etc.) and can select an event. Based on the user's selection of the event, the host device can perform a facial analysis of the video streams and/or images associated with that event based on that user's facial image data. If the host device identifies a video stream and/or image including the user (e.g., with a predetermined probability), the host device can provide such video streams and/or images to the user.

While the method 300 is described above as sending and/or receiving video streams, image data, contextual data, etc. and presenting and/or sharing user-specific video streams and/or image data with one or more users, it should be understood that a system can be arranged such that video stream data and/or image data can be captured in any suitable manner, analyzed by any suitable device, and sent to and/or shared with any suitable user or user device. By way of example, in some instances, a user can manipulate a user device (e.g., client device such as the client device 150) to capture a facial image of the user. For example, the user can open a mobile application (e.g., when the user or client device is a smartphone or other mobile or wearable electronic device) and can capture a facial image (e.g., a "selfie") via a camera of the client device. In other words, the user can control the camera of the client device via the application to capture a selfie. Such a selfie can be provided to register a user such that the application can identify facial recognition data (e.g., facial feature characteristics) of the user. This facial recognition data can be used to identify the user in subsequently received videos and/or images.

In some instances, the user can capture content (e.g., image data and/or a video stream) via the application. As described above, the content can be a video stream of one or more people in a given context such as, for example, one or more people at a sporting event or the like. In some instances, the user captured (e.g., generated) content can be associated with contextual data such as a time, date, location, venue, event, etc. and/or can otherwise be tagged with data and/or metadata. In other instances, the user generated content need not be associated with contextual data. The user generated content (e.g., video stream data or the like) can be analyzed via facial recognition and/or other image analysis via the client device or a host device to determine the presence of any registered user (e.g., any user with a user profile stored in the database). If a registered user is identified in the video stream, the user, the client device, and/or the host device can define a user-specific video stream associated with one or more of the identified users. The user, the client device, and/or the host device can then determine whether to share the user-specific video stream with each identified user. In some instances, the sharing of the user-specific video stream(s) can be automatic based on a user-profile and/or preference and/or based on a setting or the like within the mobile application or account. In other instances, the sharing of the user-specific video stream(s) can be based on a manual or other input from the user (e.g., based on a selection or the like). In still other instances, the sharing of the user-specific video stream(s) can be based on a peer networking session, in which each user (or each client device used in the peer networking session) receives a user-specific video stream. In this manner, the user generated content (e.g., the user captured video stream and/or image data) can be captured, analyzed, and/or shared in a similar manner as those described herein.

Figure 4:
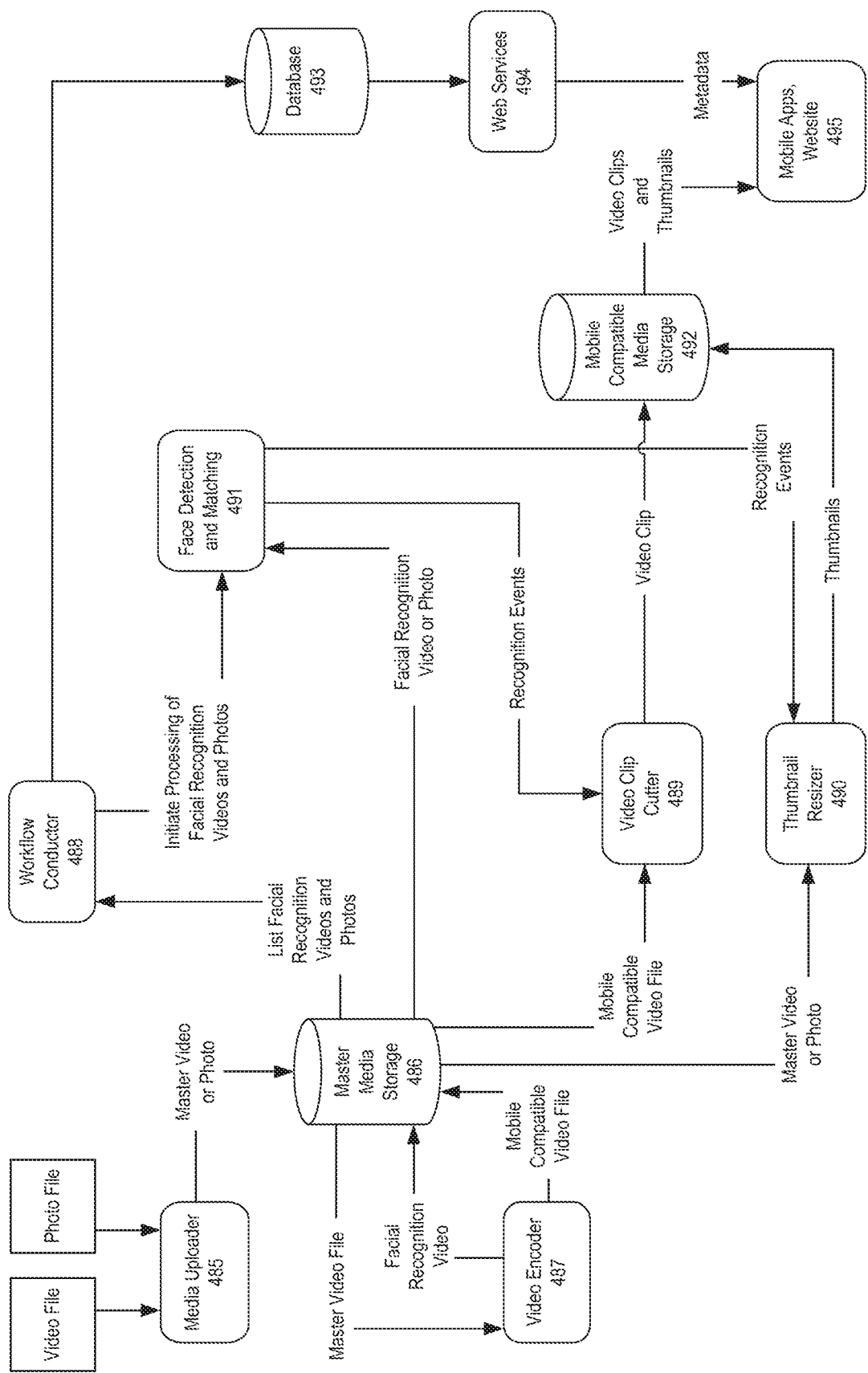
FIG. 4 is a flowchart illustrating a method of using a video recognition system according to another embodiment.

FIG. 4 is a flowchart illustrating a method of presenting a contextual video stream to, for example, a mobile device associated with a user according to an embodiment. In some instances, a video file(s) and/or a photo file(s) can be uploaded to a media uploader 485. The media uploader 485 can be any suitable device configured to receive and/or process video and/or image files such as, for example, the host device 110 described above with reference to FIGS. 1A, 1B and 2. A master video and/or photo file is then stored in a master media storage 486. The master media storage 486 can be any suitable storage device. For example, the master media storage 486 can be included in and/or a part of memory included in the media uploader 485. In other embodiments, the master media storage 486 can be a database or the like such as, for example, the database 140 described above with reference to FIGS. 1A and 1B.

In some instances, the master video file can be sent from the master media storage 486 to a video encoder 487. The video encoder 487 can be any suitable device or portion of a device configured to convert the master video file into one or more desired formats. For example, as shown in FIG. 4, the video encoder 487 can convert the master video file into a facial recognition video and a mobile-compatible video file, each of which are stored in the master media storage 486. A list of one or more facial recognition video files and/or photo files is then sent to a workflow conductor 488, which can prioritize, organize, and/or otherwise control an order in which files are subsequently processed and can send a signal operable in initiating processing of the facial recognition video file(s) and/or photo file(s) to a face detection and matching processor 491 (e.g., a processor, module, device, etc. such as, for example, the analysis module 121 described above with reference to FIG. 2), as described in further detail herein. In addition, an indication associated with the workflow can be sent from the workflow conductor 488 to a database 493, which can store the indication associated with the workflow and that can send data associated with the indication to a web service processor 494 (e.g., an Internet website service provider, processor, module, and/or device), as described in further detail herein.

As shown in FIG. 4, the mobile compatible video file is sent from the master media storage 486 to a video clip cutter

489, which can also receive data associated with recognition events, as described in further detail herein. The master video file or photo file is sent from the master media storage 486 to a thumbnail resizer 490, which can also receive data associated with the recognition events, as described in further detail herein. The facial recognition video or photo file(s) is/are sent from the master media storage 486 to the face detection and matching processor 491, which in turn can perform any suitable facial recognition process to define the recognition events. Moreover, the face detection and matching processor 491 can analyze and/or process the facial recognition video and/or photo file in accordance with the priority and/or order defined by the workflow conductor 488.

As described above, data associated with the recognition events can then be sent from the face detection and matching processor 491 to the video clip cutter 489 and the thumbnail resizer 490. The video clip cutter 489 can be any suitable processor, module, and/or device that can receive the mobile-compatible video file and that can subsequently trim, cut, extract, separate, and/or otherwise define a video clip associated with the recognition events of a user within the facial recognition video and/or photo. The video clip associated with the recognition event of the user can then be sent from the video clip cutter 489 to a mobile-compatible media storage 492. The thumbnail resizer 490 can be any suitable processor, module, and/or device that can receive the master video and/or photo file(s) and that can subsequently define one or more thumbnails (e.g., small images with a relatively small file size, which in turn, can be associated with and/or indicative of a larger image and/or video). In this embodiment, the thumbnails can be associated with and/or indicative of the recognition events and can be sent from the thumbnail resizer 490 to the mobile-compatible media storage 492.

As shown in FIG. 4, the video clips and the thumbnails can be sent from the mobile-compatible media storage 492, for example, to one or more mobile applications and/or websites 495. For example, in some instances, the video clips and thumbnails can be sent to an Internet server or the like, which in turn, can present the video clips and thumbnails on a website or the like. In other instances, the video clips and thumbnails can be sent to a client device associated with the user, which in turn, can present the video clips and thumbnails on a display (e.g., when a mobile application is opened, selected, running, etc.). Moreover, metadata (e.g., user identity, identity of event, location of event, location of a client device, etc.) or the like associated with the indication of the workflow (described above) can be sent from the web services processor 494 to the mobile application and/or websites 495. In this manner, a video clip of a user and any contextual and/or metadata associated therewith can be sent to and/or accessed by the user via a mobile application and/or website.

Figure 5:
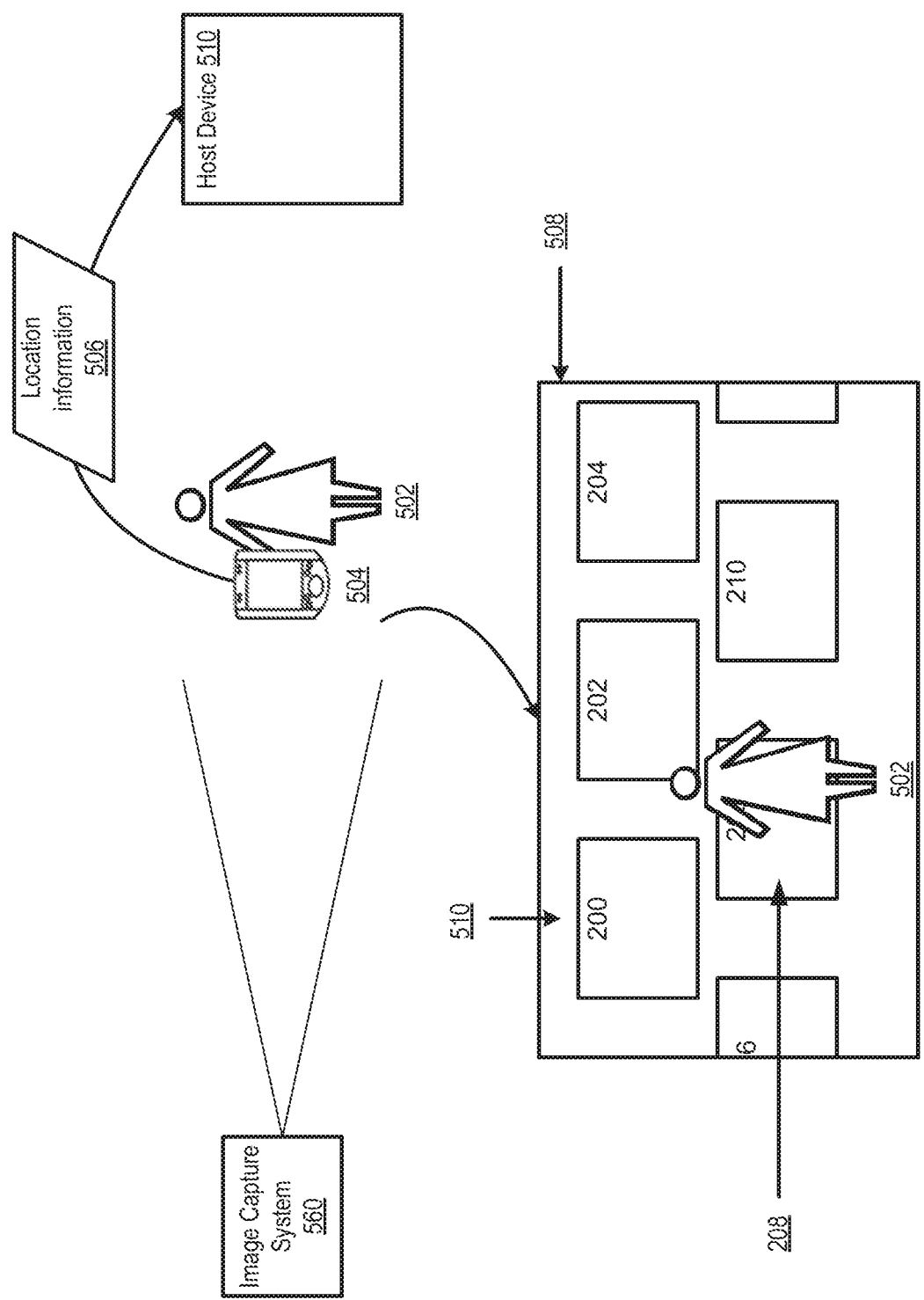
FIG. 5 is an illustration of an image capture device capturing contextual information in media, according to an embodiment.

FIG. 5 is an illustration of an image capture system 560 (e.g., similar to image capture system 160 shown in FIG. 1) capturing contextual information in media, according to an embodiment. Initially, the image capture system 560 can capture images and/or video of a venue. The image capture system 560 can identify characteristics such as background landmarks, unique features of the walls, floor, design elements, furniture, and/or the like within the images and/or video of the venue. The image capture system 560 can send these characteristics (also referred to herein as landmark data and/or information) to the host device 510 and the host device 510 can store this information (e.g., within a database). The host device 510 can store this information associated with location information of the venue. Similarly stated, the host device 510 can store the landmark information such that it is associated with that landmark's location within the venue.

In some implementations (as described in FIGS. 1-4), the image capture system 560 can capture media (e.g., a video stream, photographs, and/or other media) including a user 502. The user 502 can use a mobile device 504 including a mobile application configured to send location data 506 (e.g., Global Positioning System (GPS) coordinates, Wi-Fi signal indicating being within range of an access point, NFC signal information, Bluetooth communications indicating being within range of an iBeacon, cellular triangulation information, cognitive network switching and protocol information that estimates a distance from a point of content capture, location data associated with a position in a venue such as a seat number or section, and/or like location data) to the host device 110, e.g., when the mobile device detects a signal and/or Wi-Fi network associated with a venue. In some implementations, the mobile application can be configured to interact with an iBeacon (and/or a similar device configured to transmit information to other devices), and can be configured to send location data to the host device 110 (e.g., such as the iBeacon identifier, mobile device GPS data, and/or other such information).

Media 508 (e.g., photographs, videos, and/or related media files) captured by the image capture system 160 can include an image or video of the user 502, as well as buildings, features of the venue, objects, background landmarks, and/or other aspects of the background 510 of the scene. For example, the media can include not only the user 502, but seats next to the user 502 at a sports venue, landmarks in the background of the media and associated with a particular location (e.g., within a venue), signs, and/or other such information (e.g., unique features of the walls, floor, design elements, furniture, etc.). The host device 110 can use the background with the user's location data to further verify that the user 502 is likely to appear in the media. More specifically, in some instances, an analysis module of host device 510 (e.g., similar to analysis module 121 shown in FIG. 2) can perform image processing on the video stream, e.g., to extract scenery and/or other background, non-person data from the video stream (also referred to as landmark data). For example, the analysis module can use image processing techniques to detect a seat number 200 in the media. A location module of the host device 510 (e.g., similar to 124 shown in FIG. 2) can match the extracted data to location data in the database (e.g., using metadata, keywords, and/or image processing of previously-stored location images) to estimate a location of the video stream. For example, the location module can use the seat number 200 to estimate the seat 514 at which the user 502 appears to sit in the media, and can determine an approximate location at which the media was captured based on the location of the seat within the venue. For another example, the location module can compare the landmark data in the video stream to the images and/or video previously captured and stored by the host device 510. Because of the association between the location and the landmark data stored by the host device 510, the host device 510 can identify a location of the video stream.

In some instances, a user can also check into the venue. Specifically, the user's mobile device can send a message including location information for the user (e.g., the GPS coordinates of the user's mobile device, an identifier for an iBeacon, NFC tag, cellular network, Wi-Fi and/or other network, and/or similar device in close proximity to the mobile device, and/or the like). The location module can store the location data in the user's account data. After the location module has determined a location of the video stream and of the user, the location module can compare the seat 208 to the location data provided by the user's mobile device to determine the likelihood the user 502 was actually sitting in the seat 208. For example, the location module can retrieve records of users whose most recent location data closely matches the estimated location of the media (e.g., whose most recent location data is within a predetermined number of meters from the estimated location of the media, and/or the like). For each user record retrieved, the analysis module can perform facial recognition on the media, e.g., using the user's image data for comparison, to determine whether the user appears in the media. Based on this information, the host device can determine a list of users whose image could have been captured in the media in a particular location, and can determine, from this reduced pool of users, whether a positive match between persons in the media, and any of the users 502 in the list of users, has been made. In some instances, facial recognition can then be performed for the image to identify which users from the reduced pool of users (e.g., the users identified as being in the general area based on landmark information and/or user device location information) are identified in the media. Reducing the pool of users using landmark data and user device location information reduces the number of false positives when using facial recognition. In some implementations, the host device can use the facial recognition analysis, and location data, to determine whether or not to store and/or discard (e.g., delete and/or not store) the video stream in the database. In other implementations, the host device can store the video stream, regardless of whether or not the video stream can be matched with a particular user. The host device can then associate the video stream with a particular user when the user device location, and when facial recognition data associated with the user, are used in combination with the landmark and/or other location data, to determine whether or not the user can be identified in the video stream.

Figure 6:
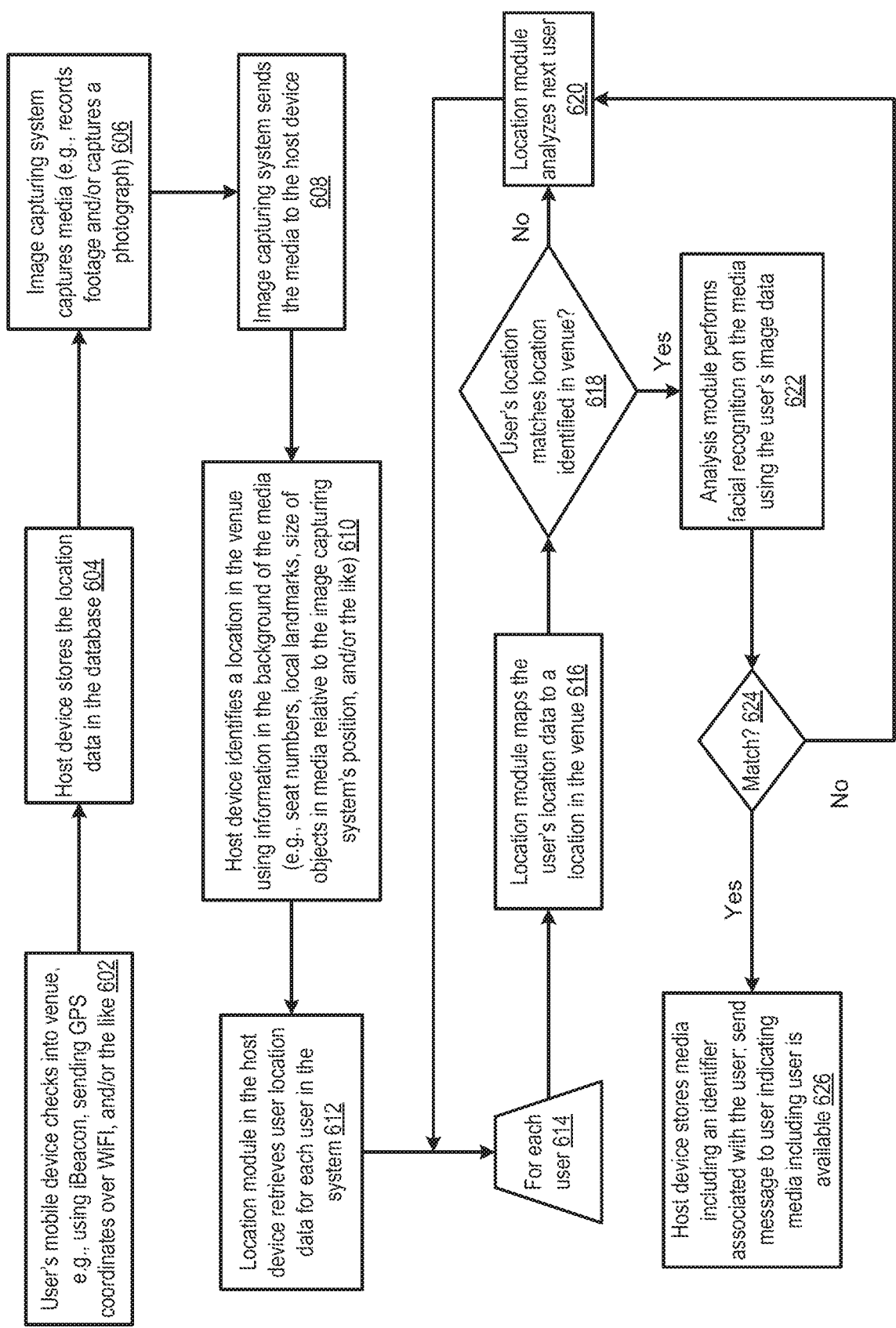
FIG. 6 is a logic flow diagram illustrating using contextual information in media, and location data, to identify a user in the media, according to an embodiment.

FIG. 6 is a logic flow diagram that illustrates using contextual information in media, and location data, to identify a user in the media, according to an embodiment. In some implementations, for example, the user's mobile device 504 can "check-in" to a venue and/or other location at 602 (e.g., by sending location data and/or iBeacon identifiers to the host device 110 (shown in FIG. 1)). This can provide the venue and/or a host device associated with the a video recognition system (e.g., host device 110 of FIG. 1) an indication that the user is within the venue and/or at the event. In addition, this can provide an indication of a user's location within the venue and/or at the event. In some implementations, the mobile device 504, via the mobile application stored on the device, can be configured to periodically send updated GPS data to the host device 110, and/or can be prompted to send location data to the host device 110 when the mobile device 504 comes within close proximity to an iBeacon, Wi-Fi hotspot and/or similar device. The host device 110 can store 604 the location data in the database 140.

In some implementations, instead of the user's mobile device checking in, a ticket sales and/or ticket processing device at a venue can send a message to the host device 110 indicating that a user has bought and/or used a ticket for a particular event at the venue, the time at which the ticket was purchased and/or redeemed, and/or the like. In other implementations, a user's location can be inferred, e.g., based on previously-stored location data for the user, based on tickets the user has bought for events at particular venues, and/or the like.

An image capture system 160 (shown in FIG. 1) can capture media (e.g., including but not limited to recording video footage and/or capturing at least one photograph), at 606, and can send the media to the host device 110 (shown in FIG. 1), at 608. The image capture system 160 can also send its location data (e.g., GPS coordinates for the image capture system 160, and/or the like) to the host device 110. The host device 110 can identify a location in the media, at 610 (e.g., using landmark data in the scenery and/or background of the media). For example, in some implementations, the host device 110 (e.g., via analysis module 121 shown in FIG. 1) can use image recognition processing techniques to detect particular objects in the background (seats, local landmarks, and/or the like), to detect identifying information in the background (e.g., signs, seat numbers, venue features, and/or the like), and/or to estimate a distance between the image capture device 160 and the user 502 (e.g., by using the size of objects in the media, relative to the image capturing system's location and/or the user 502, to estimate the distance). The host device 110 (e.g., via location module 124) can then use the identifying information, objects, and/or distance to identify the location captured in the media. For example, if the analysis module 121 detects a seat number in a sports venue, the location module 124 can use the image capture system's location data to determine in which sports venue the image capture system 160 is located, and can retrieve a map of the venue and/or other data to determine where in the venue a seat with the seat number would be located. As another example, the location module 124 can detect a national landmark (e.g., a famous statue) and/or a state sign, and can determine a GPS location for the user based on known location data for the national landmark and/or state sign. If the image capture device 160 provides location data, the location module 124 can verify the detected location based on the location data from the image capture device.

In some implementations, the location module 124 can also determine a location based on other media previously stored at the host device 110. For example, the image capture system 160 can record a video including a famous statue, and the location module 124 can determine the GPS coordinates for the statue and store said coordinates, e.g., as metadata for the video data as stored in the database 140. If the image capture device 160 later sends subsequent media that also includes the statue, the location module 124 can detect, using image processing techniques similar to those disclosed herein, the identity of the statue using the previously-received video data, and can determine the location of the statue using the previous video data (e.g., via metadata stored with the video data, and/or the like). For another example, the location module can use pre-captured image data of landmarks within a venue that associates the landmarks with a location within the venue to identify the location within the venue captured in the media.

The location module 124 can then retrieve user location data (e.g., GPS data, iBeacon data, ticket purchase data, and/or the like) for users in the database 140 at 612. For each user 614, the host device can map the user's location data to a location in the venue and/or at the event at 616. For example, if the user location data indicates that the user is at a particular sports venue, the location module 124 can map the user's location data to a location within the venue, e.g., using a map of the venue and/or similar data. The location module 124 can then determine 618 whether or not the user's location in the venue matches the location the location module 124 identified in the media. For example, the host device 110 can determine whether a seat number detected in the media matches a seat number close to the iBeacon identified in a user mobile device's check-in message, and/or whether the seat number is in close proximity to a seat number associated with the user's ticket. If the two locations do not match, the location module 124 determines that the user is likely not at the location where the media was recorded, and the location module 124 can analyze 620 the location data of the next user.

If the two locations match, the analysis module 121 (e.g., shown in FIG. 2) can perform facial recognition 622 on the media, e.g., using the user's previously-stored image data and the media received from the image capturing system 160. If the analysis module 121 detects a match 624 between the user and a person in the media, the host device can store 626 the media (e.g., including metadata such as the location at which the media was recorded, an identifier associated with the user, and/or other information). The host device 110 can then notify the user (e.g., via an email, a text (e.g., Short Message Service (SMS) and/or Multimedia Messaging Service (MMS)) message, a mobile device application notification, and/or the like) that the image capture system 160 captured media including the user. The user can then access the media. If the two locations do not match, the analysis module may not perform the facial analysis, and may end the process of matching the user to the media.

In some implementations, the location module 124 can perform the location analysis before preforming facial recognition on the media. In other implementations, the host device 110 can perform the location analysis after performing facial recognition on the media. Performing the location analysis before the facial recognition can reduce the number of comparisons made (thus reducing the amount of time and resources used to perform the facial recognition), and can reduce the amount of data retrieved and processed from the database 140. This can also reduce the number of false positives produced from the facial recognition process since the facial recognition analysis can be performed on those individuals whose location matches the location of the image and not on the individuals whose location does not match the location of the image.

In some instances, a facial recognition confidence score can be calculated based on the location information identified by the landmark data in the media. For example, if a landmark in the media indicates the video is of a specific portion of a venue and a user's device indicates the user is within that portion of the venue, the confidence score that the user is within the media can increase. Conversely, if a landmark in the media indicates the video is of a specific portion of a venue and a user's device indicates the user is not within that portion of the venue, the confidence score that the user is within the media can decrease. Thus, while not limiting the number of individuals on which facial recognition is performed, the landmark data can reduce false positives by affecting the confidence scores of users.

While described above as being used in conjunction with facial recognition, in other embodiments, the location information received from the user's device and the location information derived from the landmark data in the image and/or video can be used without facial recognition to identify a user in the video. Specifically, for example, the location module (e.g., shown in FIG. 2) can determine using information in the video (e.g., using information in the scenery and/or background of the media) a location of the video. If a user device indicates that a user is at that specific location, the user can be identified as being included in the video. The video can then be provided to the user, as described above.

While described above as receiving location information from an image capture device (e.g., a position with the venue), in other embodiments such location information is not received and the location of the image capture device can be identified solely based on the landmark data in the media (e.g., using information in the scenery and/or background of the media). In such embodiments, image capture devices not associated with the video recognition system (e.g., video recognition system 100 of FIG. 1) and/or image capture devices not communicatively coupled with the video recognition system can be used to capture images and/or videos. The location of such images can be identified without location specific data (other than the image itself) being provided by the image capture device.

While various embodiments have been described above, it should be understood that they have been presented by way of example only, and not limitation. For example, while the embodiments and methods have been described herein as defining a contextual video stream of a user at an event or the like and sending the contextual video stream to a client device and/or otherwise allowing access to the contextual video stream via, for example, a web browser and the Internet, in other embodiments, a host device can store, in a database, any number of contextual video streams associated with a user. In some instances, the host device can be configured to define a user profile or the like that can include any number of contextual video streams of the user. In some instances, the user can access his or her user profile via a mobile application, a computer application, a web browser and the Internet, and/or the like. Moreover, in some instances, the user can share or otherwise request the host device to share any number of contextual video streams of the user with a different user and/or via a social media site. In some instances, a user can allow access to a portion of his or her user profile such that other users can view the contextual video streams included therein.

While specific examples have been particularly described above, the embodiments and methods described herein can be used in any suitable manner. For example, while the system 100 is described above as defining a contextual video stream of a user at a sporting event, in other embodiments, the methods described herein can be used to identify an individual using, for example, facial recognition and video analytics in any suitable setting, venue, arena, event, etc. For example, in some embodiments, the methods described above can be used to capture a contextual video stream at a concert, a rally, a graduation, a party, a shopping mall, a place of business, etc. In one example, a host device can receive a contextual video stream from, for example, a graduation. In some instances, as described above, the host device can perform any suitable facial recognition and/or video analytics to identify the graduate (and/or any individual and/or user). Moreover, the host device can be configured to analyze contextual information such as, a user profile associated with the graduate, an order of students walking across the stage, location data associated with the graduate's client device, and/or any other suitable data. As such, the host device can analyze the data to verify the identity graduate (e.g., when the data satisfies a criteria(ion)) and can define a contextual video stream of the graduate, for example, as he or she walks across the stage to receive a diploma or the like. In other instances, the host device can identify a family member or friend of the graduate and can define a contextual video stream of him or her in a similar manner.

While the embodiments have been described above as being performed on specific devices and/or in specific portions of a device, in other embodiments, any of the embodiments and/or methods described herein can be performed on any suitable device. For example, while the contextual video streams have been described above as being sent to a host device (e.g., the host device 110) for facial recognition and/or image analysis, in other embodiments, any suitable analysis can be performed on or at a client device. For example, in some instances, a user can capture a video stream (e.g., a contextual video stream) via a camera of the client device and in response, the client device can analyze the video to identify any number of registered users or the like in the video stream. In some instances, the analysis can be via a convolutional neural net sent to and/or stored on the client device (e.g., stored in memory and associated with the system application). In some instances, the analysis can be pre-processed and/or pre-sorted based on, for example, the user's contact list, friends list, established connections, etc., as described above. In some instances, the client device can send a user-specific video stream to any identified user, as described above. In other embodiments, the client device can upload and/or send the analyzed video stream and/or the user-specific video stream(s) to the host device 110 and/or the database 140.

While video streams and/or image data is described above as being "contextual," it should be understood that the video stream data and/or image data can be independent of and/or unassociated with "contextual data." For example, in some instances, a user can capture a video stream and/or image and can upload the video stream and/or image for processing without defining and/or sending contextual data associated with the video stream and/or image data. In some instances, a host device or the like (e.g., the host device 110) can receive the user-generated video stream and/or image data and in response, can perform one or more facial recognition processes and/or any other suitable analytics on the data to define, for example, a user-specific video stream or user-specific image that is independent of contextual data.

While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above. While specific methods of facial recognition have been described above according to specific embodiments, in some instances, any of the methods of facial recognition can be combined, augmented, enhanced, and/or otherwise collectively performed on a set of facial recognition data. For example, in some instances, a method of facial recognition can include analyzing facial recognition data using Eigenvectors, Eigenfaces, and/or other 2-D analysis, as well as any suitable 3-D analysis such as, for example, 3-D reconstruction of multiple 2-D images. In some instances, the use of a 2-D analysis method and a 3-D analysis method can, for example, yield more accurate results with less load on resources (e.g., processing devices) than would otherwise result from only a 3-D analysis or only a 2-D analysis. In some instances, facial recognition can be performed via convolutional neural nets (CNN) and/or via CNN in combination with any suitable two-dimensional (2-D) and/or three-dimensional (3-D) facial recognition analysis methods. Moreover, the use of multiple analysis methods can be used, for example, for redundancy, error checking, load balancing, and/or the like. In some instances, the use of multiple analysis methods can allow a system to selectively analyze a facial recognition data set based at least in part on specific data included therein.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™ Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

What is claimed:

1. An apparatus, comprising:
 a memory; and
 a processor in communication with the memory,
 wherein the processor is configured to:
  receive data from a user device and save the data in a user profile including facial recognition data of a user associated with the user device,
  receive at least one image from an image capture device,
  identify a venue based at least in part on data associated with the at least one image and an image location within the venue based at least in part on image characteristics within the at least one image, and
  determine whether the user is at the venue based on data stored in the user profile,
  when the user is determined to be at the venue, determine a user location within the venue based on data stored in the user profile,
  perform facial recognition analysis on the at least one image with respect to facial recognition data within the user profile if the user location is within a predetermined distance of the image location, and
  associate the at least one image with the user profile data structure when the at least one image matches the facial recognition data,
 and wherein the processor configured to not perform facial recognition analysis on the at least one image with respect to the facial recognition data of the user if the distance is greater than the predetermined distance.

2. The apparatus of claim 1, wherein the data received from the user device is at least one of iBeacon data, Global Positioning Service (GPS) data, a seat identifier, social media data, internet web browsing data, purchase data, near field communication (NFC) verification data, cellular network triangulation data, or a Wi-Fi network identifier.

3. The apparatus of claim 1, wherein the user is a first user, the image capture device is at least one of a manually operated camera associated with the venue, an autonomous camera associated with the venue, or a camera of a user device associated with a second user different from the first user.

4. The apparatus of claim 1, wherein the processor is configured to identify the image location by:
 performing image processing on the at least one image;
 identifying at least one venue landmark based on the image processing; and
 identifying the image location by determining a location of the venue landmark.

5. The apparatus of claim 1, wherein the facial recognition data of the user includes data relating to at least one photograph of the user that is stored in the user profile.

6. The apparatus of claim 1, wherein the processor is configured to
 determine a facial recognition confidence score associated with the user,
 increase the facial recognition confidence score when the user location within the venue and the image location are within the predetermined distance of each other, and
 associate the at least one image with the user profile if the facial recognition confidence score associated with the user meets the predetermined criterion.

7. The apparatus of claim 6, wherein the processor is configured to automatically send to the user device the at least one image when the facial recognition confidence score meets the predetermined criterion.

8. The apparatus of claim 1, wherein the processor is configured to determine the user location within the venue by inferring a section within the venue based on data stored in the user profile.

9. The apparatus of claim 1, wherein the data stored in the user profile includes location data, the processor is configured to determine the user is at the venue based on the location data stored in the user profile.

10. The apparatus of claim 1, wherein the data stored in the user profile includes historical location data associated with the user device, and the processor is configured to determine the user is at the venue based on the historical location data stored in the user profile.

11. The apparatus of claim 1, wherein the data stored in the user profile includes location data and non-location data, and the processor is configured to determine the user is at the venue based on the location data and configured to determine the user location within the venue based on the non-location data.

12. A method, comprising:
 storing data received from a user device in a user profile;
 receiving at least one image from an image capture device;
 identifying (1) a venue based at least in part on data associated with the at least one image and (2) an image location within the venue based at least in part on image characteristics within the at least one image;
 determining a user is at the venue based on data stored in the user profile;
 determining a user location within the venue based on data stored in the user profile;
 performing facial recognition analysis on the at least one image with respect to facial recognition data within the user profile if the user location is within a predetermined distance of the image location and not performing the facial recognition analysis if the distance is greater than the predetermined distance, and
 associating the at least one image with the user profile when the at least one image matches the facial recognition data.

13. The method of claim 12, wherein the data received from the user device is at least one of iBeacon data, Global Positioning Service (GPS) data, a seat number, social media data, internet web browsing data, purchase data, near field communication (NFC) verification data, cellular network triangulation data, or a Wi-Fi network identifier.

14. The method of claim 12, further comprising:
 pre-processing the at least one image to determine contextual information before the performing facial recognition analysis on the at least one image,
 the contextual information including at least one of an identifier associated with the venue, a time the at least one image was captured, or a coinciding event that occurred when the at least one image was captured.

15. The method of claim 12, further comprising:
 calculating a confidence level associated with the user based on the performing facial recognition analysis on the at least one image with respect to the facial recognition data; and
 determining that the facial recognition data associated with the user matches a likeness of the user in the at least one image when the confidence level exceeds a predetermined threshold.

16. The method of claim 12, wherein the at least one image is a video including the at least one image, the method further comprising:

dividing the video into a series of images, the performing facial recognition analysis on the at least one image includes performing facial recognition analysis on each image in the series of images with respect to the facial recognition data.

17. The method of claim 12, further comprising:

sending a signal indicative of an instruction to graphically render the at least one image at the user device when the at least one image matches the facial recognition data.

18. The method of claim 12, wherein the identifying the image location includes identifying the image location based at least in part on background scenery or a background landmark included in the at least one image.

19. The method of claim 12, wherein the user profile is from a plurality of user profile data structures stored in the database, each user profile from the plurality of user profile data structures including facial recognition data of a corresponding user, the method further comprising:

discarding the at least one image if the at least one image does not match facial recognition data of at least one user profile from the plurality of user profile data structures.

20. The method of claim 12, further comprising:

sending, automatically and to the user device, the at least one image when the at least one image matches the facial recognition data.

21. The method of claim 12, wherein determining the user location within the venue includes inferring a section within the venue based on the data in the user profile.

22. The method of claim 12, wherein the data stored in the user profile includes location data, and determining the user is at the venue includes determining the user is at the venue based on the location data.

23. The method of claim 12, wherein the data stored in the user profile includes location data and non-location data, determining the user is at the venue includes determining the user is at the venue based on the location data, and determining the user location within the venue includes determining the user location within the venue based on the non-location data.

* * * * *